(12) United States Patent
Urakawa

(10) Patent No.: US 12,193,921 B2
(45) Date of Patent: Jan. 14, 2025

(54) DISPOSABLE WEARING ARTICLE

(71) Applicant: Daio Paper Corporation, Ehime (JP)

(72) Inventor: Wataru Urakawa, Tochigi (JP)

(73) Assignee: Daio Paper Corporation, Ehime (JP)

( * ) Notice: Subject to any disclaimer, the term of this patent is extended or adjusted under 35 U.S.C. 154(b) by 1101 days.

(21) Appl. No.: 16/629,535

(22) PCT Filed: May 1, 2018

(86) PCT No.: PCT/JP2018/017397
§ 371 (c)(1),
(2) Date: Jan. 8, 2020

(87) PCT Pub. No.: WO2019/064667
PCT Pub. Date: Apr. 4, 2019

(65) Prior Publication Data
US 2020/0214903 A1   Jul. 9, 2020

(30) Foreign Application Priority Data

Sep. 27, 2017   (JP) .................. 2017-187178

(51) Int. Cl.
  A61F 13/496   (2006.01)
  A61F 13/49   (2006.01)
  A61F 13/51   (2006.01)
  B29C 65/00   (2006.01)
  B29L 31/48   (2006.01)

(52) U.S. Cl.
  CPC ............ *A61F 13/496* (2013.01); *A61F 13/49* (2013.01); *A61F 13/49011* (2013.01);
  (Continued)

(58) Field of Classification Search
  CPC ............ B29L 2031/4878; A61F 13/496; A61F 13/49; A61F 13/49011; A61F 13/51;
  (Continued)

(56) References Cited

U.S. PATENT DOCUMENTS 5,507,895 A   4/1996  Suekane
5,576,090 A   11/1996  Suzuki
(Continued)

FOREIGN PATENT DOCUMENTS

CN   107205859 A   9/2017
CN   114450154 A * 5/2022
(Continued)

OTHER PUBLICATIONS

International Search Report and Written Opinion for PCT/JP2018/017397, mailed Jun. 12, 2018.

*Primary Examiner* — Susan S Su
*Assistant Examiner* — Erin A Kim
(74) *Attorney, Agent, or Firm* — Andrus Intellectual Property Law, LLP

(57) ABSTRACT

A disposable wearing article is provided with a laminated stretchable structure excellent in peeling strength and flexibility. The disposable wearing article has a laminated stretchable structure, in which an elastic sheet of a thermoplastic resin is laminated between a first sheet layer made of nonwoven fabric and a second sheet layer made of nonwoven fabric. The first sheet layer and the second sheet layer are bonded through through-holes formed on the elastic sheet at a large number of bonded portions arranged at intervals. In the bonded portions, the first sheet layer and the elastic sheet are melt-solidified, and a layer forming at least a surface opposite to the elastic sheet in the second sheet layer is not melt-solidified. The first sheet layer and the second sheet layer are bonded via a melt-solidified material of the first sheet layer and a melt-solidified material of the elastic sheet at the bonded portions.

14 Claims, 19 Drawing Sheets

(52) U.S. Cl.
CPC .......... *A61F 13/51* (2013.01); *B29C 66/1122* (2013.01); *B29C 66/21* (2013.01); *B29C 66/433* (2013.01); *B29C 66/7294* (2013.01); *B29C 66/81429* (2013.01); *B29L 2031/4878* (2013.01)

(58) Field of Classification Search
CPC .......... A61F 13/15699; A61F 13/15739; A61F 13/49012; B29C 66/1122; B29C 66/21; B29C 66/433; B29C 66/7294; B29C 66/81429; B29C 65/086; B29C 66/344; B29C 66/41; B29C 66/81433; B29C 66/83511; B32B 2555/02; B32B 37/144; B32B 37/0084; B32B 37/04
See application file for complete search history.

(56) References Cited

U.S. PATENT DOCUMENTS

| | | | |
|---|---|---|---|
| 5,618,366 | A | 4/1997 | Suekane |
| 6,884,494 | B1 | 4/2005 | Curro et al. |
| 2014/0130956 | A1 | 5/2014 | Floberg et al. |
| 2016/0213531 | A1* | 7/2016 | Takahashi .............. D04H 1/559 |
| 2017/0049637 | A1* | 2/2017 | Mori .................. A61F 13/51476 |
| 2017/0209314 | A1* | 7/2017 | Ishikawa ........... A61F 13/49012 |
| 2017/0297316 | A1* | 10/2017 | Kline ..................... B32B 37/12 |
| 2018/0008481 | A1 | 1/2018 | Takahashi et al. |
| 2018/0014984 | A1* | 1/2018 | Sakai .................... B29C 66/344 |
| 2018/0015709 | A1* | 1/2018 | Takeuchi ............ B32B 37/0053 |
| 2018/0042788 | A1* | 2/2018 | Kurohara ................ A61F 13/49 |

FOREIGN PATENT DOCUMENTS

| | | | |
|---|---|---|---|
| JP | H05228177 | 9/1993 | |
| JP | H06327714 A | 6/2001 | |
| JP | H06327713 A | 9/2001 | |
| JP | 2004-532758 | 10/2004 | |
| JP | 4508885 | 7/2010 | |
| JP | 4934835 | 5/2012 | |
| JP | 2014-520589 | 8/2014 | |
| JP | 2016-189826 | 11/2016 | |
| JP | 2017064222 | 4/2017 | |
| JP | 6193429 B1 * | 9/2017 | ............. A61F 13/15 |

* cited by examiner

[FIG.1]
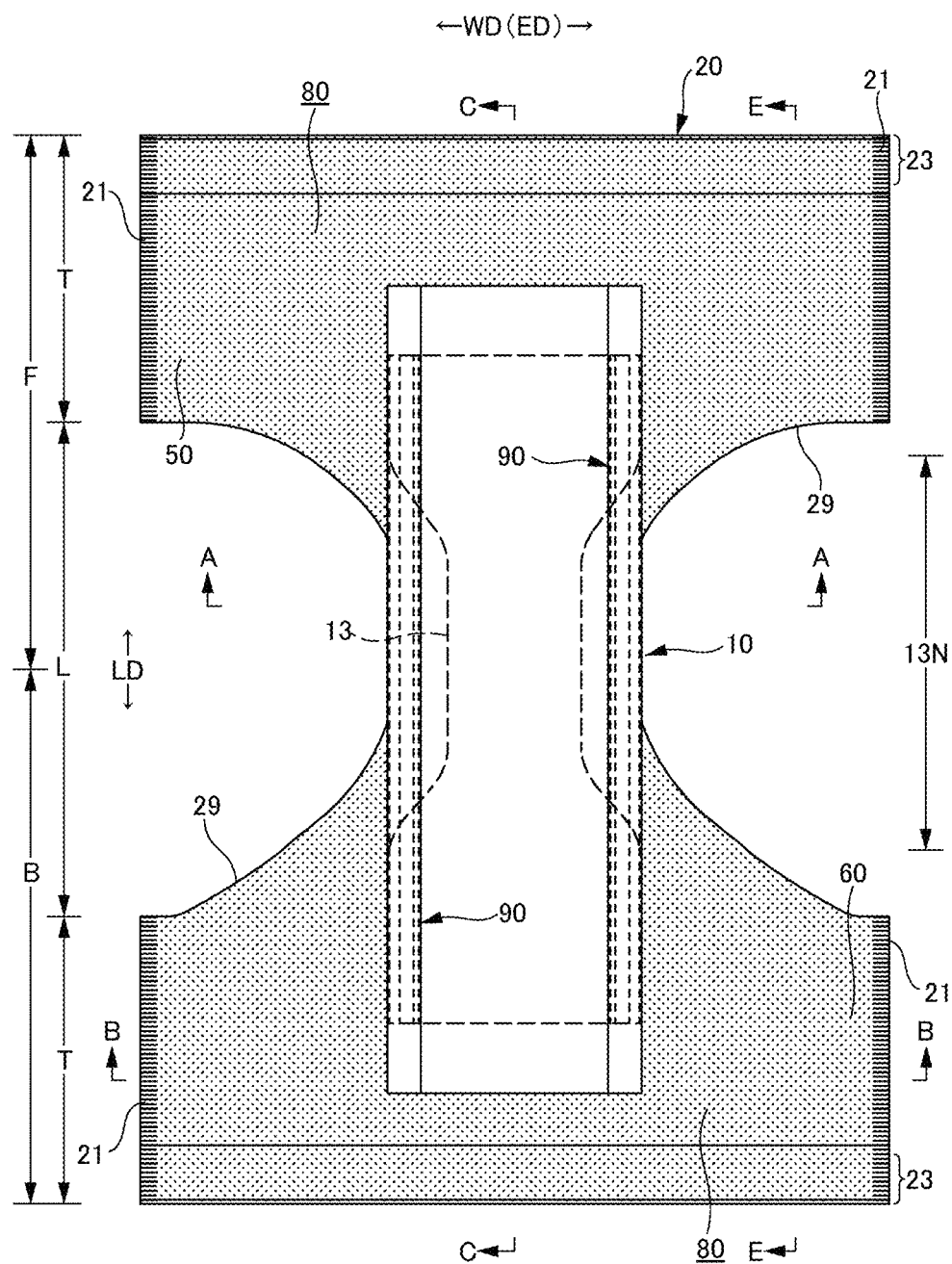

[FIG.2]
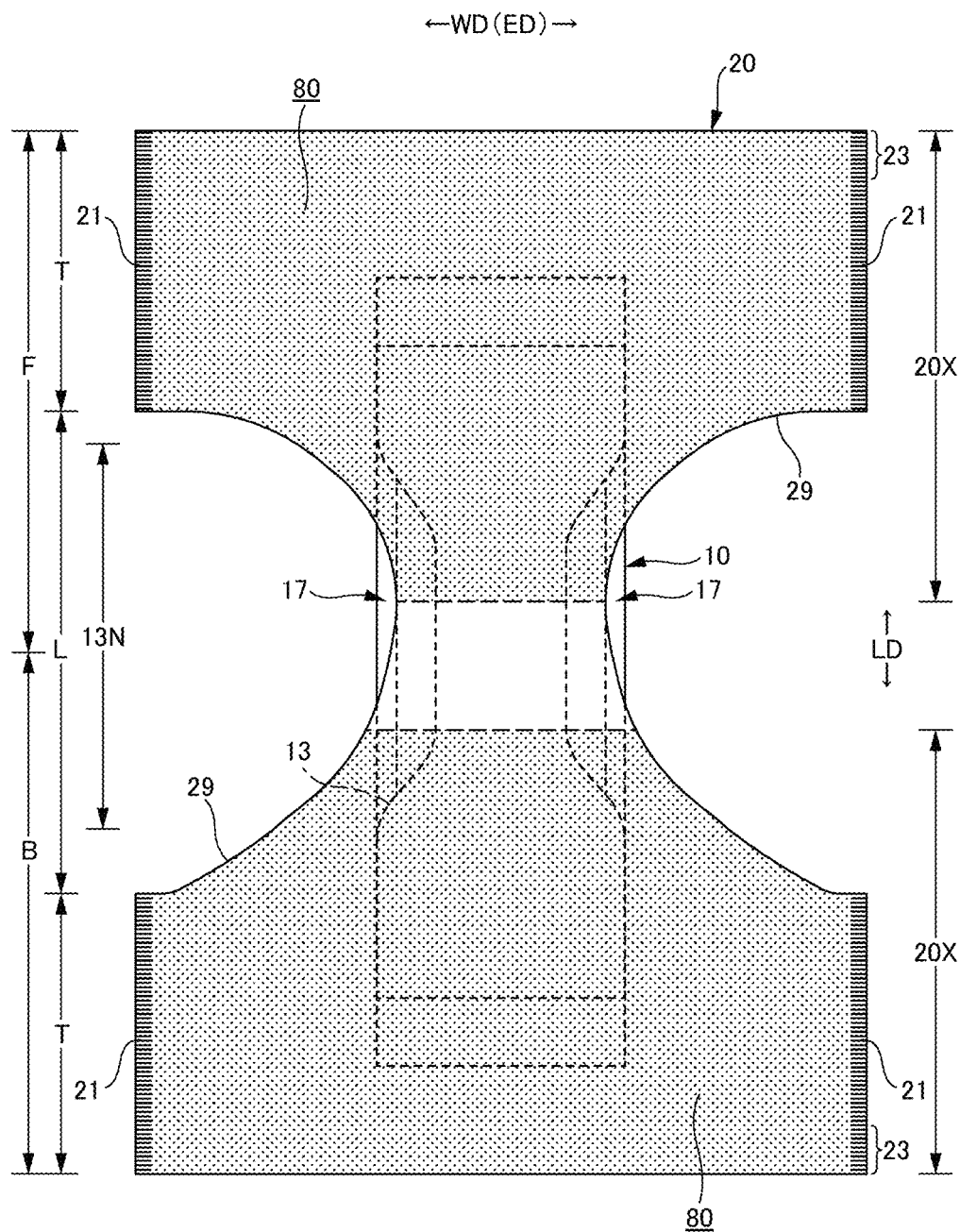

[FIG.3]
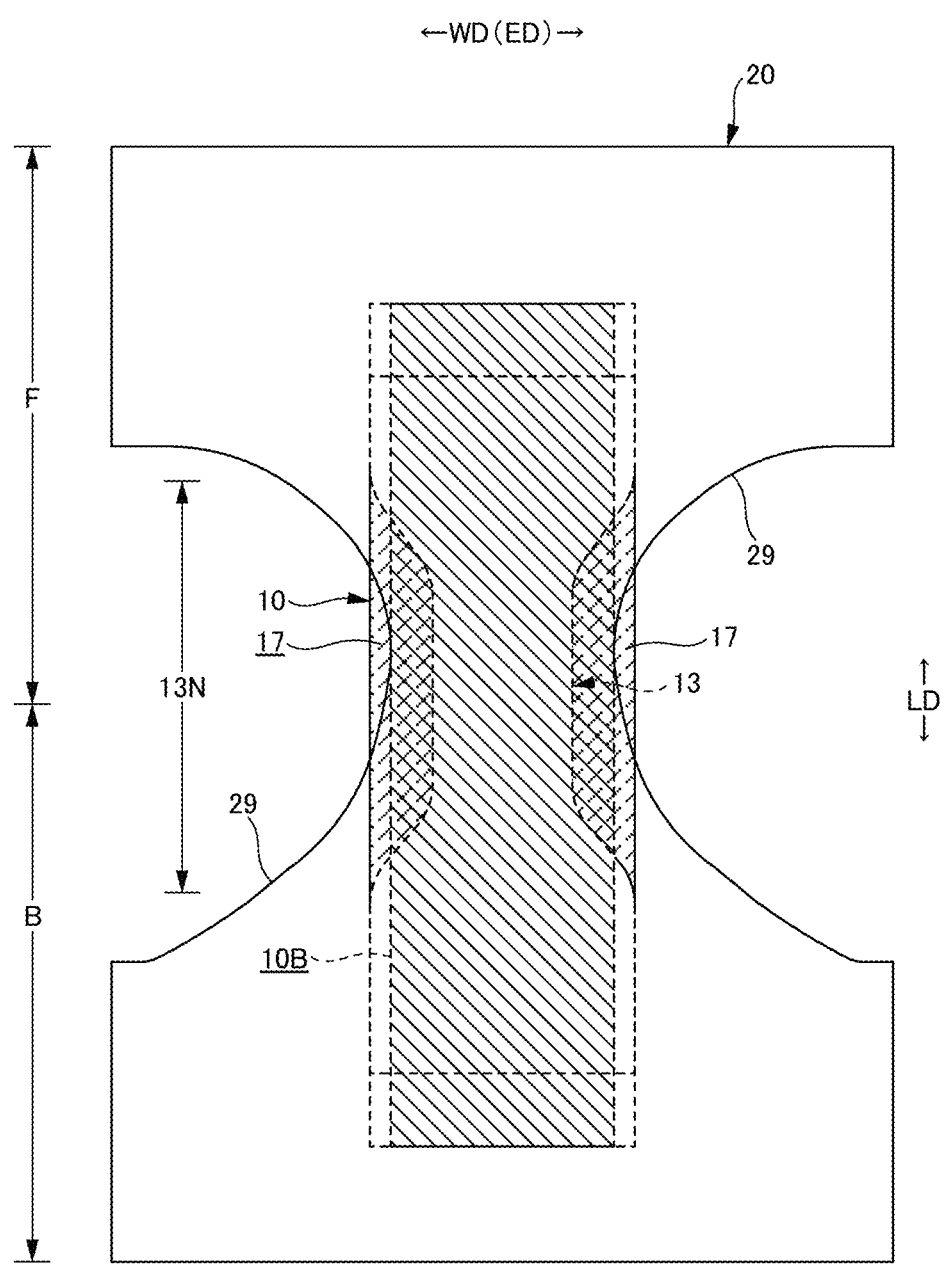

[FIG.4]
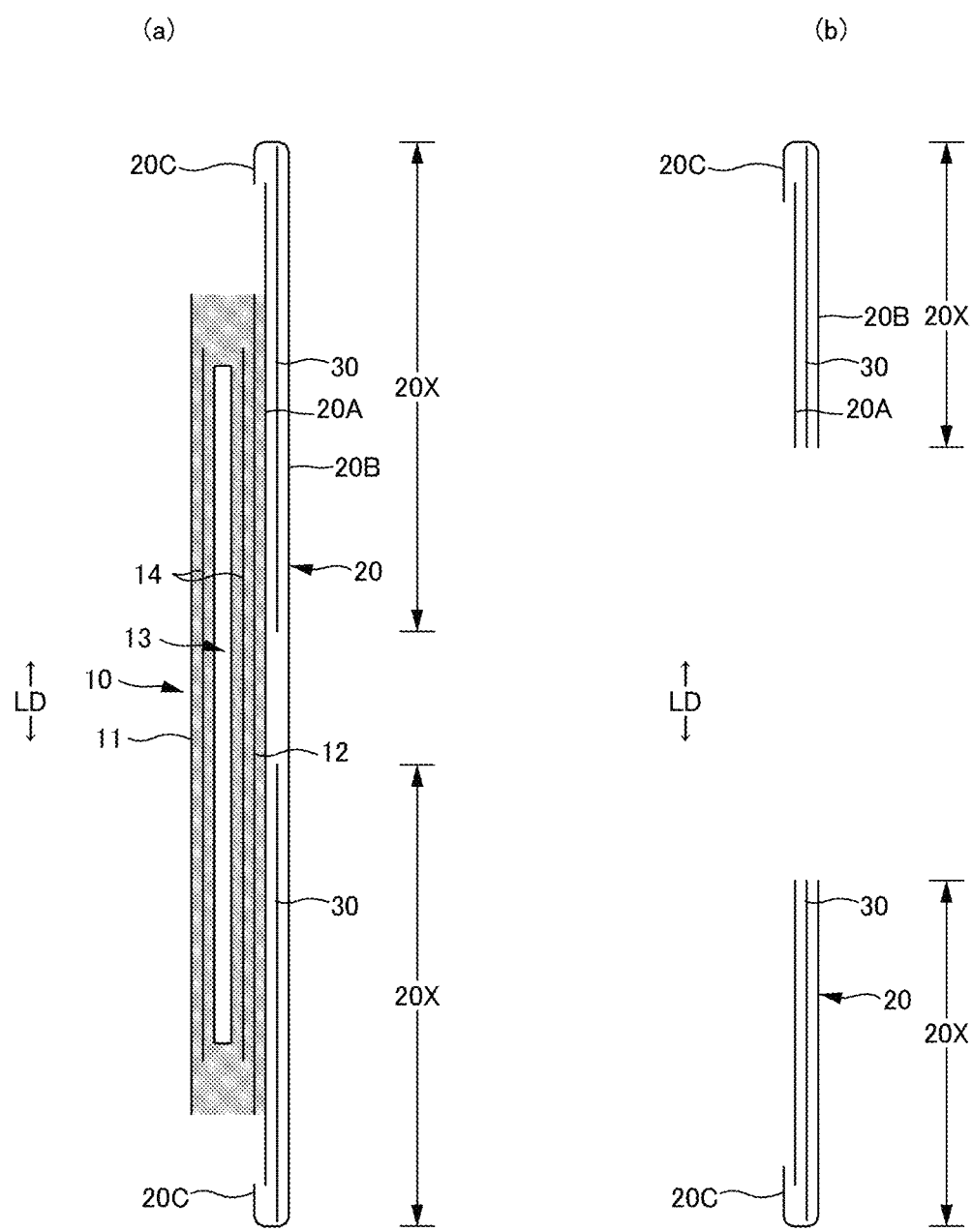

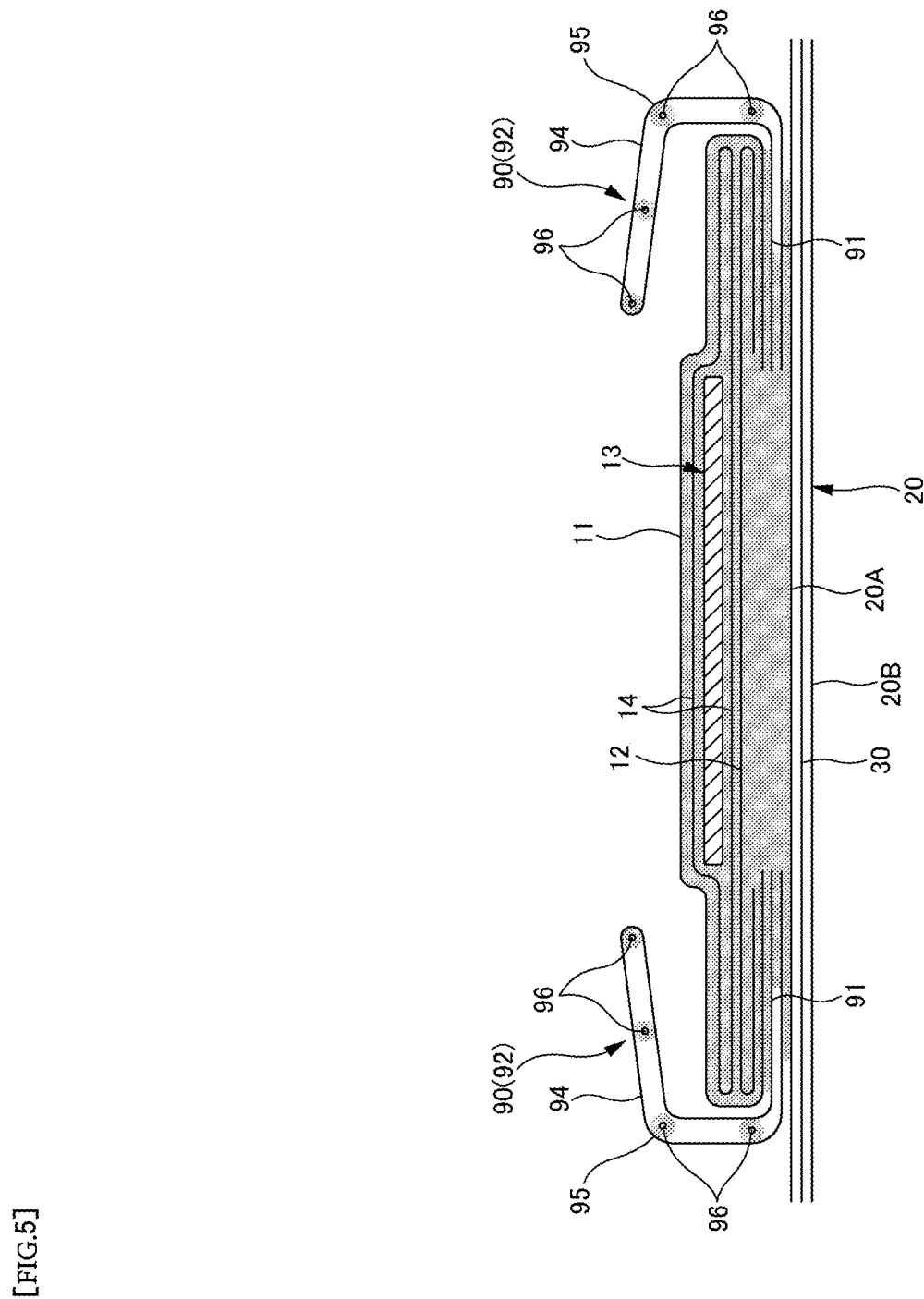
[FIG.5]

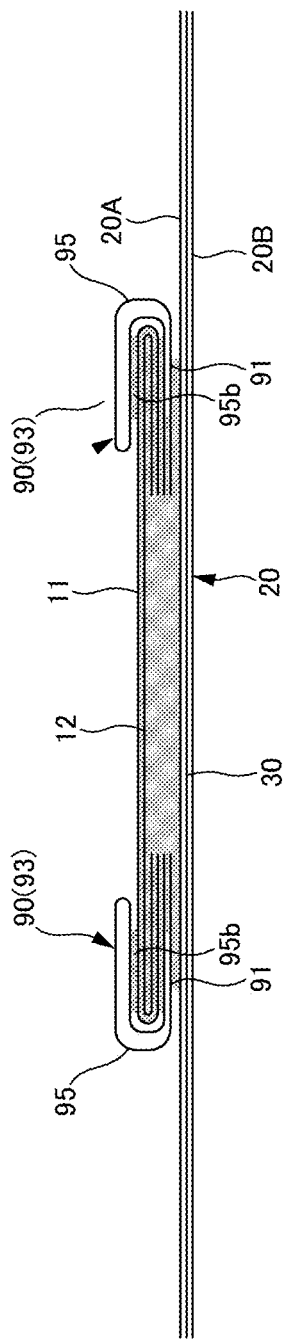
[FIG.6]

[FIG.7]
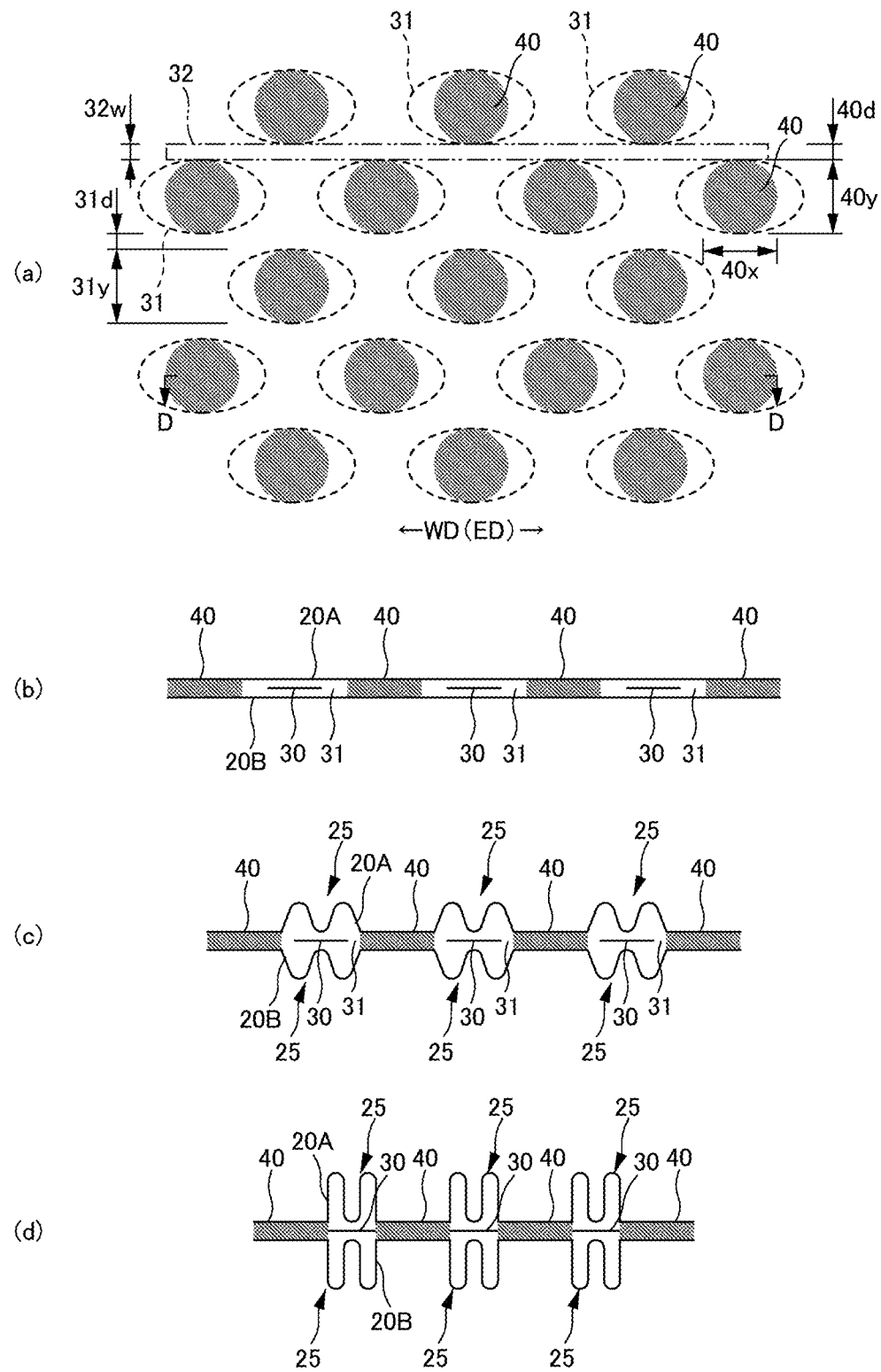

[FIG.8]
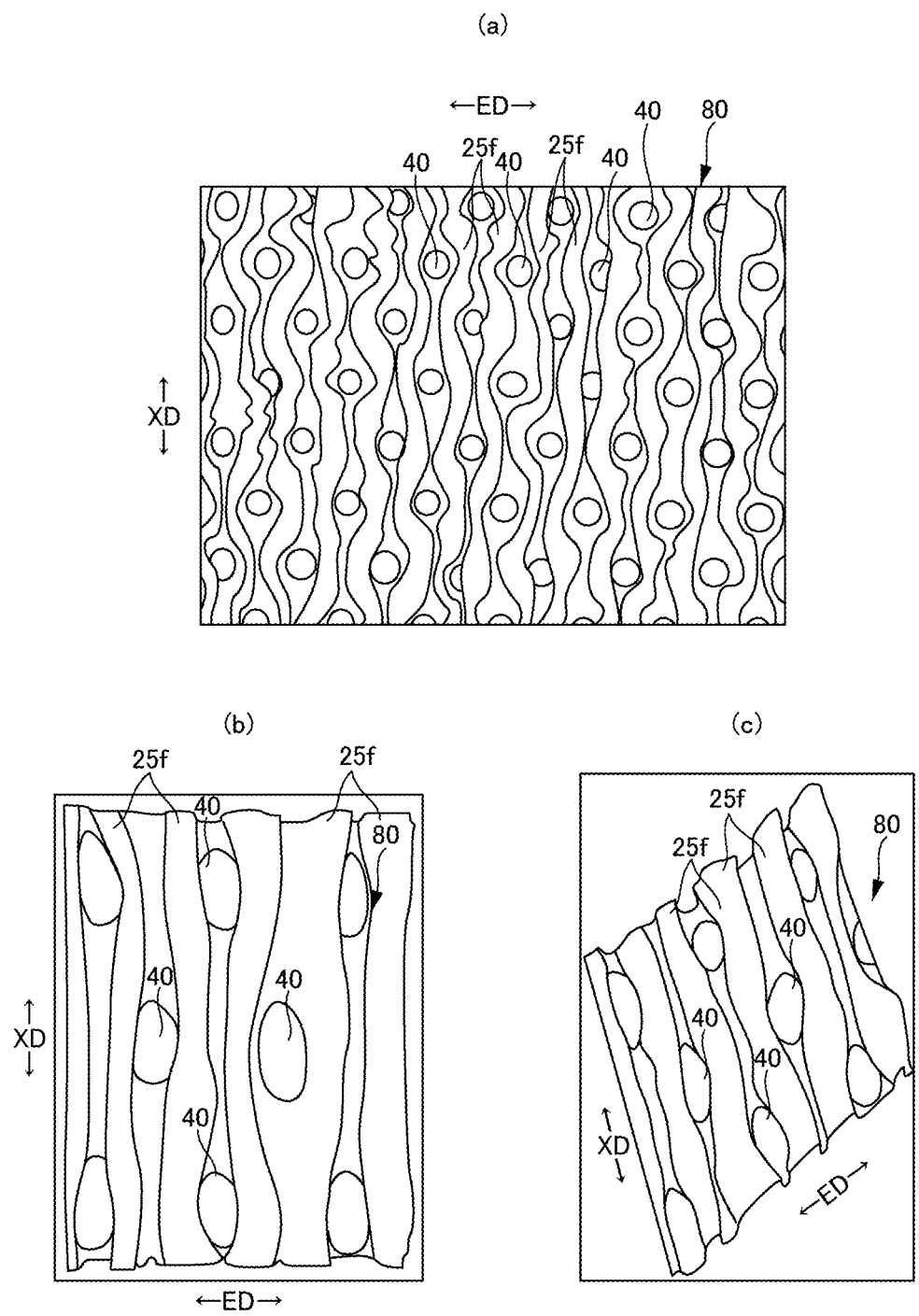

[FIG.9]
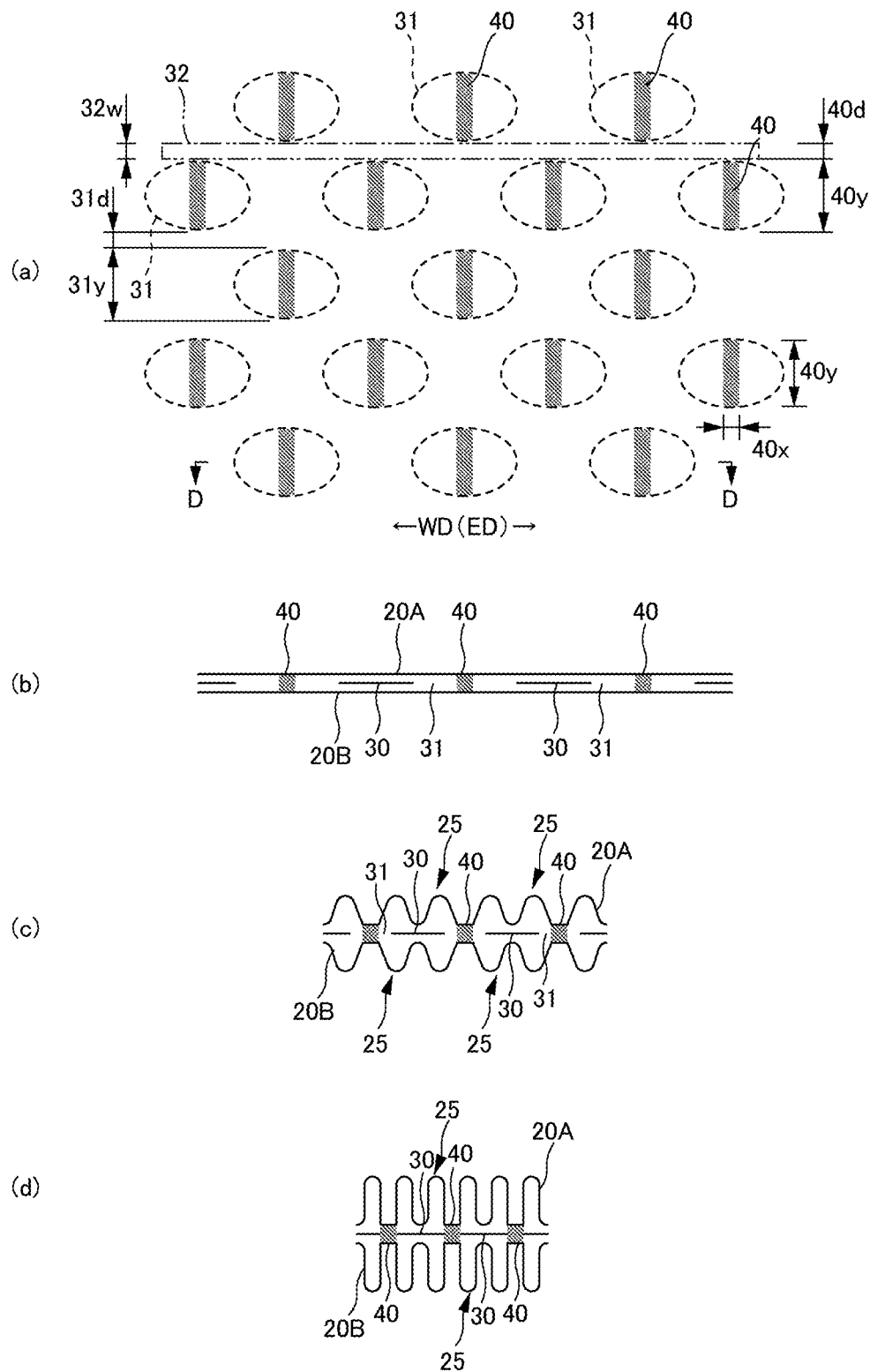

[FIG.10]
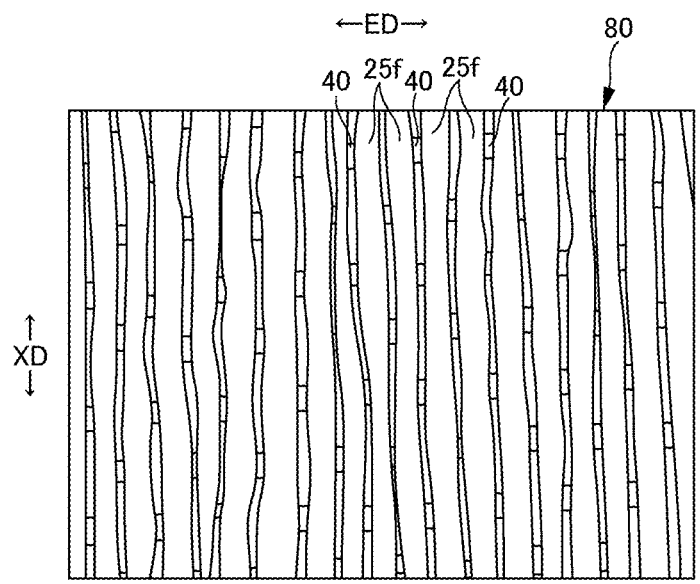
(a)
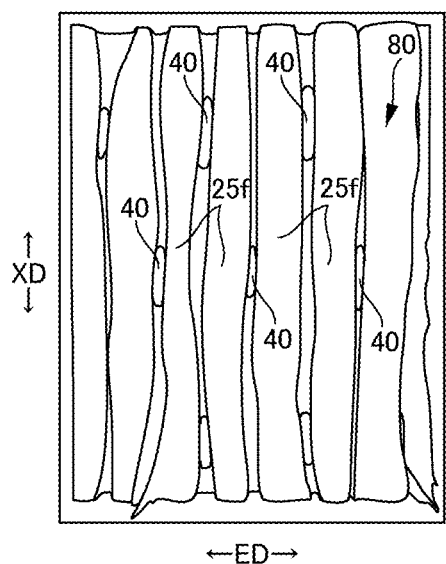
(b)
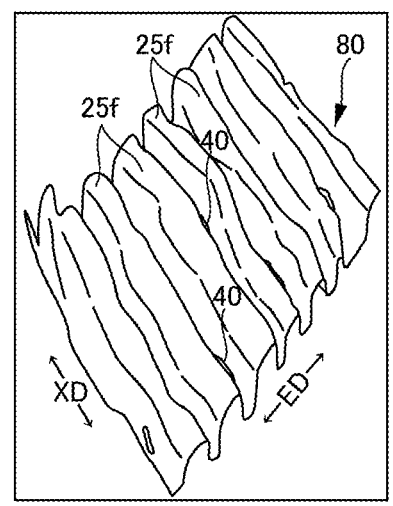
(c)

[FIG.11]
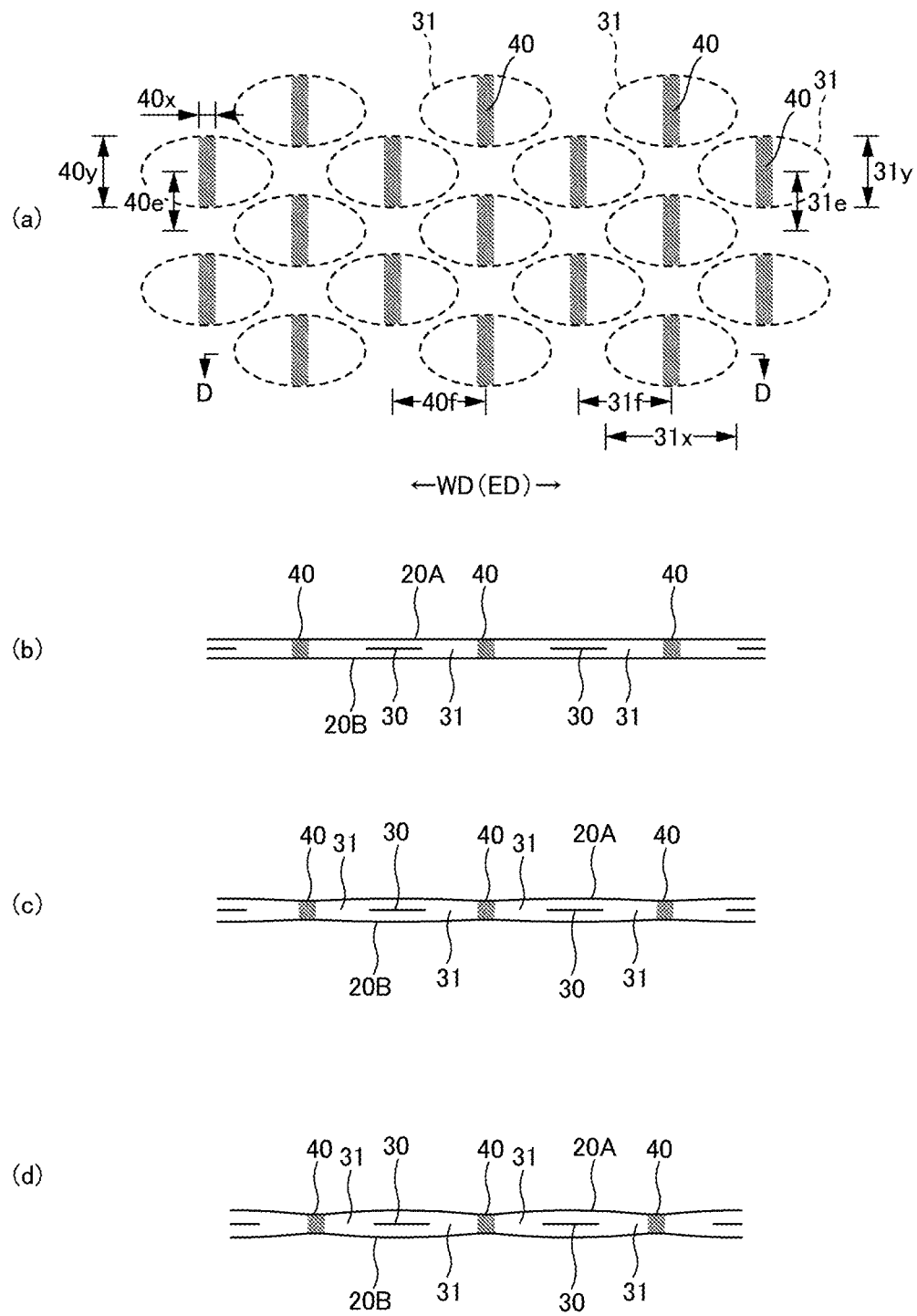

[FIG.12]
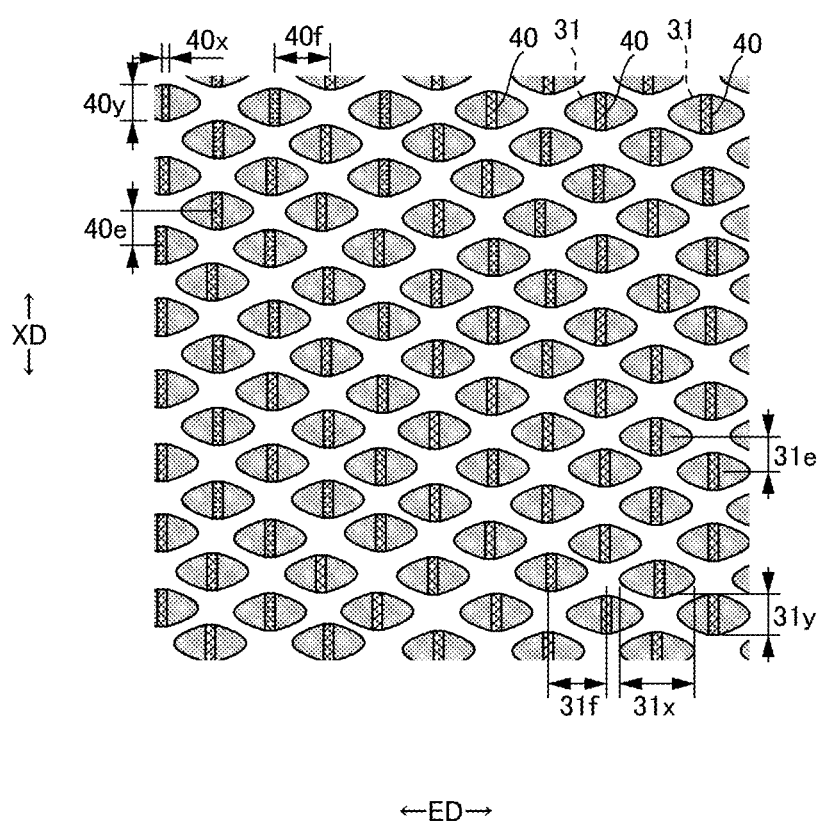

[FIG.13]
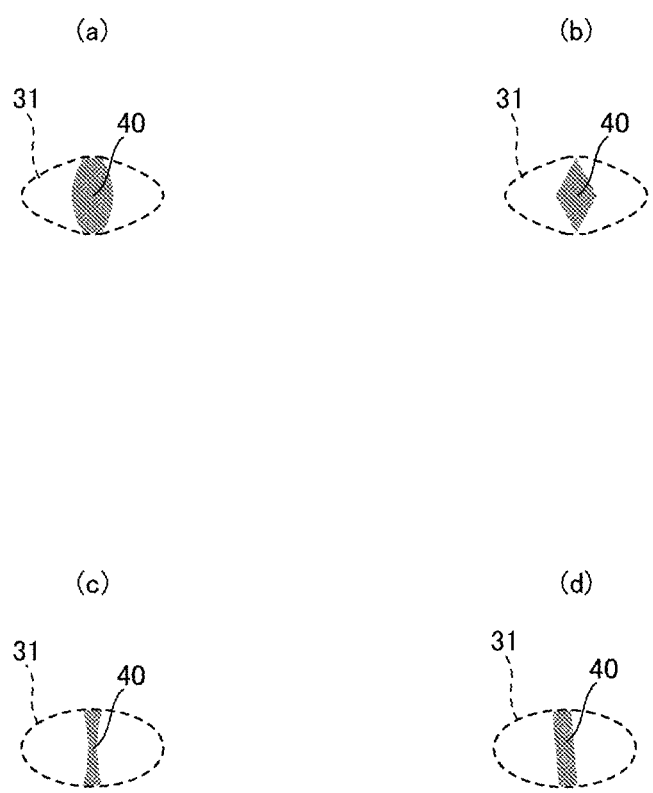

[FIG.14]
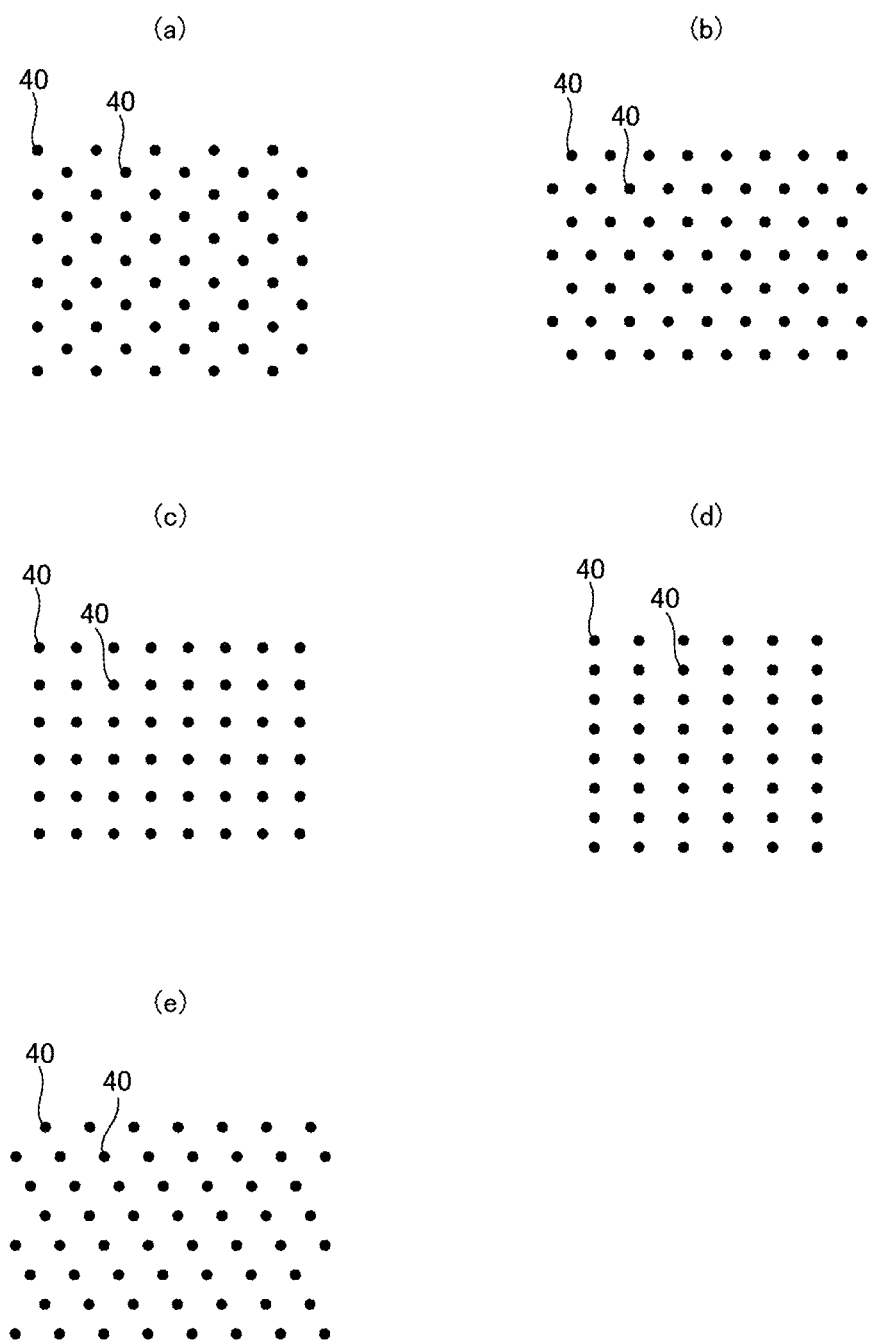

[FIG.15]
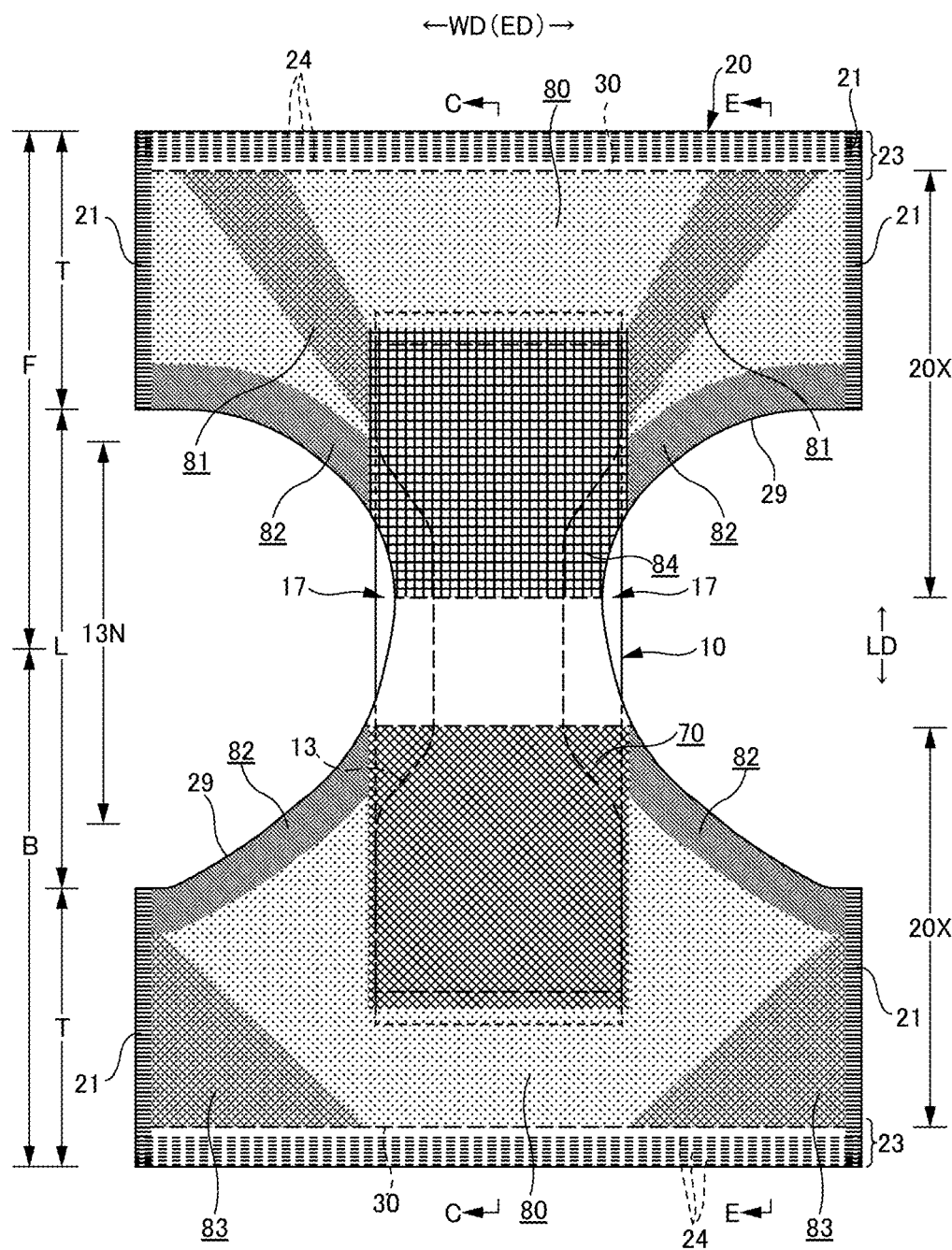

[FIG.16]
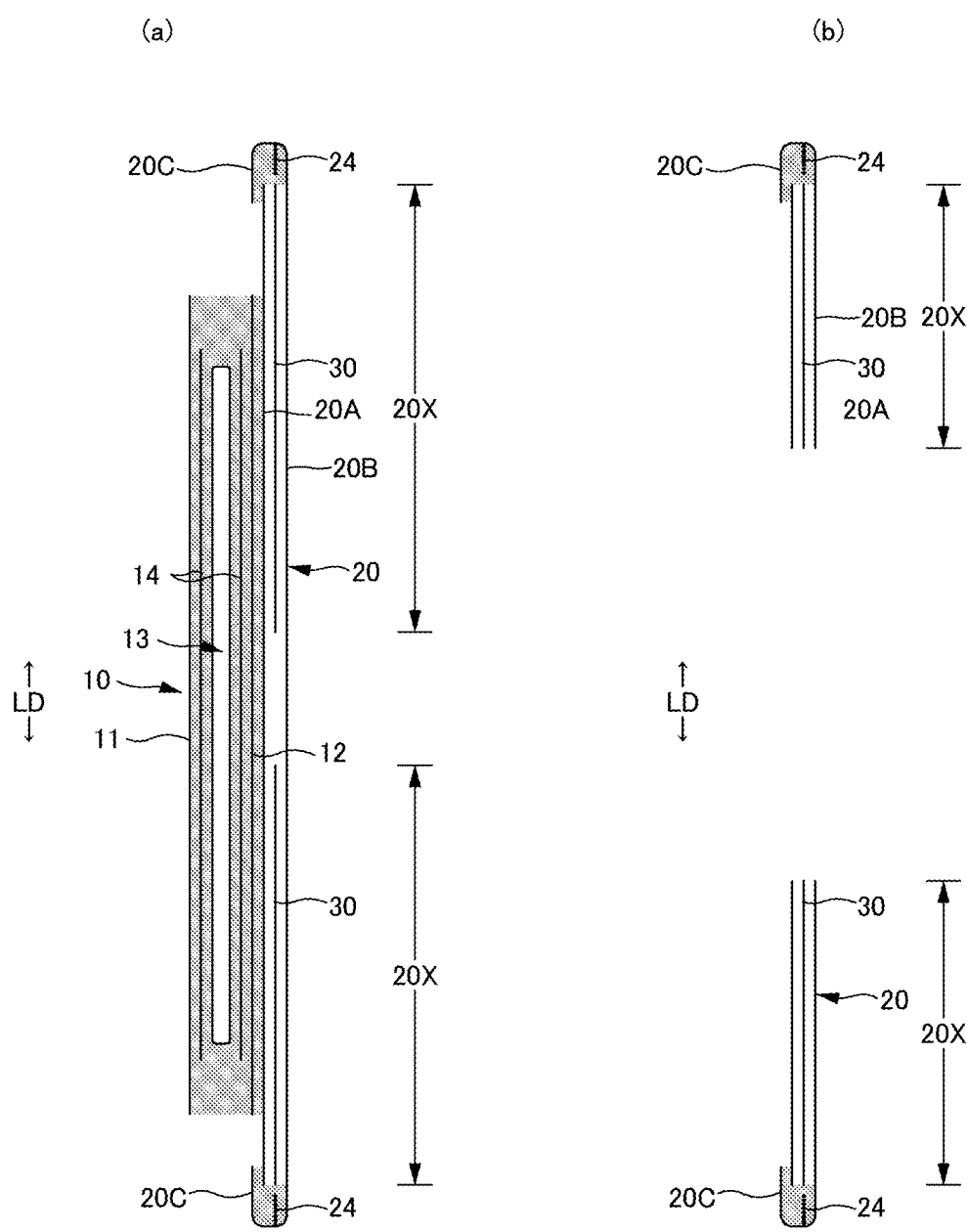

[FIG.17]
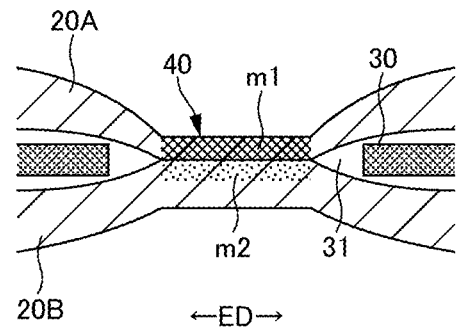
(a)
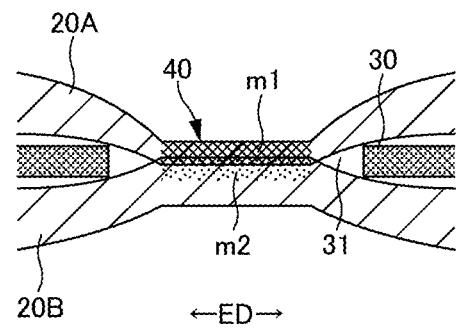
(b)
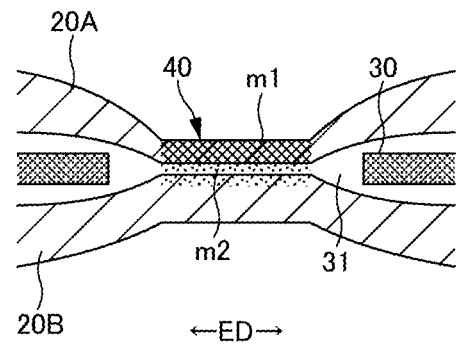
(c)

[FIG.18]
(a)
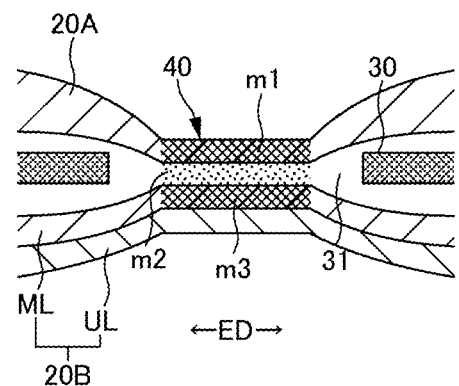
(b)
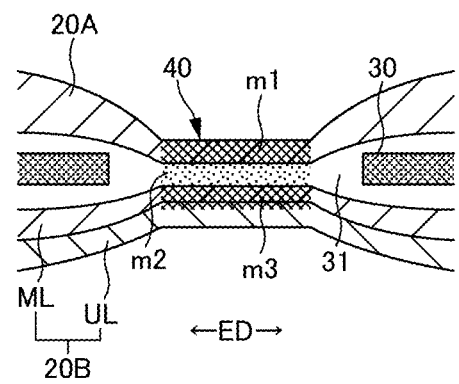

[FIG.19]
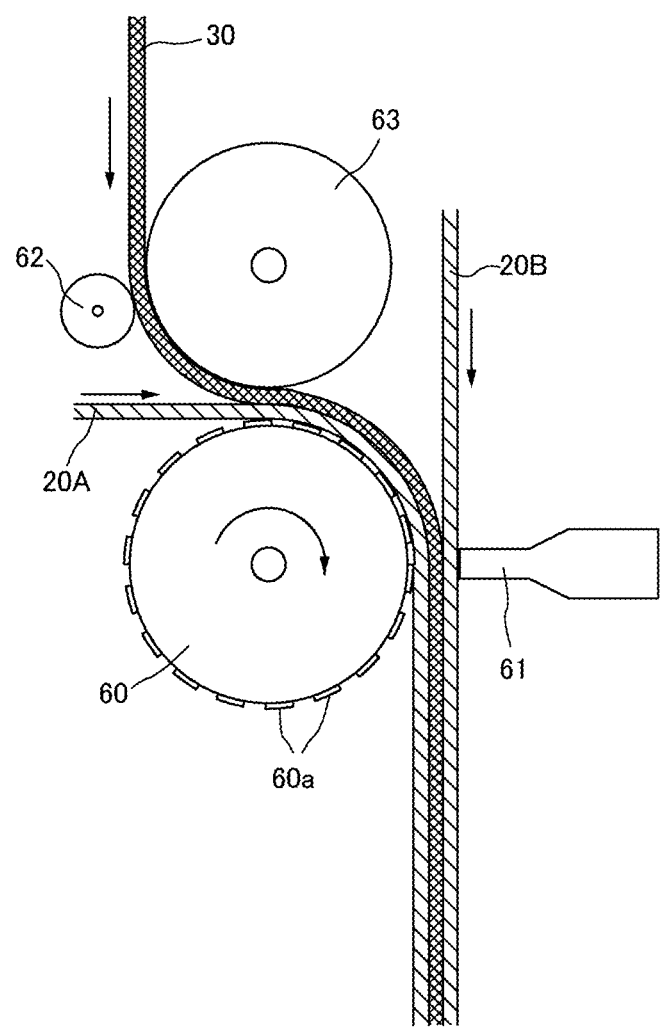

DISPOSABLE WEARING ARTICLE

CROSS-REFERENCE TO RELATED APPLICATIONS

This application is the U.S. national stage application of International Application PCT/JP2018/017397, filed May 1, 2018, which international application was published on Apr. 4, 2019, as International Publication WO 2019/064667 in the Japanese language. The International Application claims priority of Japanese Patent Application No. 2017-187178, filed Sep. 27, 2017. The international application and Japanese application are both incorporated herein by reference, in entirety.

TECHNICAL FIELD

The present invention relates to a disposable wearing article having a laminated stretchable structure in which the front and back of an elastic sheet are covered with a nonwoven fabric.

BACKGROUND ART

In absorbent articles, in order to improve fitting to the body surface, it is common to impart elasticity to appropriate positions such as around the legs and around the waist.

Conventionally, as a technique for imparting the elasticity, a technique has been widely adopted in which a large number of elongated elastic members such as rubber thread are stretched in the longitudinal direction and fixed, but as a product excellent in the surface fitting, a technique of attaching an elastic sheet in the state of being stretched in the direction of imparting the elasticity is also proposed (refer to, for example, Patent Literature 1).

In this laminated stretchable structure in which the elastic sheet is sandwiched between the sheet layers, the elastic sheet is laminated between a first sheet layer in which a stretchable region is made of a nonwoven fabric and a second sheet layer in which a stretchable region is made of a nonwoven fabric. In a state where the elastic sheets are elongated in the stretchable direction along surfaces of the elastic sheets, the first sheet layer and the second sheet layer are bonded through through-holes formed on the elastic sheet at a number of bonded portions arranged at intervals in a stretchable direction and a direction orthogonal to the stretchable direction. This laminated stretchable structure not only has excellent surface fitting but also has no bonding between the first and sheet layers and the elastic sheet, and the bonding between the first sheet layer and the second sheet layer is extremely small, and therefore it is very flexible, and there is an advantage that through-holes of the elastic sheet also contributes to improvement of air permeability.

In particular, as described in Patent Literature 1, it is preferable that the first sheet layer and the second sheet layer are bonded via a melt-solidified material of the elastic sheet since both high air permeability and high peel strength can be achieved. In particular, a structure in which the first sheet layer and the second sheet layer are melted is preferable for increasing the peel strength.

However, when the first sheet layer and the second sheet layer are melted at the bonded portion, hardening of the entire laminated stretchable structure is unavoidable, and it is difficult to achieve both the peel strength and flexibility. In addition, when the first sheet layer and the second sheet layer melt at the bonded portion, there is a problem that the melt-solidified portions are exposed on both the front and back surfaces of the laminated stretchable structure, and not only the appearance but also the touch feeling is deteriorated.

CITATION LIST

Patent Literature

Patent Literature 1: JP 2016-189826 A

SUMMARY OF INVENTION

Technical Problem

Then, the main subject of this invention is to provide a disposable wearing article provided with the laminated stretchable structure excellent in peeling strength and flexibility.

Solution to Problem

The representative aspects of the present invention that have solved the above problems will be described below.
<First Aspect>

A disposable wearing article provided with a laminated stretchable structure, in which an elastic sheet is laminated between a first sheet layer made of nonwoven fabric and a second sheet layer made of nonwoven fabric, and the first sheet layer and the second sheet layer are bonded through through-holes formed on the elastic sheet at a large number of bonded portions arranged at intervals.

In the bonded portions, one sheet layer of the first sheet layer and the second sheet layer and the elastic sheet are melt-solidified, and a layer forming at least a surface opposite to the elastic sheet in the other sheet layer of the first sheet layer and the second sheet layer is not melt-solidified, and the first sheet layer and the second sheet layer are bonded via a melt-solidified material of the one sheet layer and a melt-solidified material of the elastic sheet at the bonded portions.
(Function and Effect)

In the present aspect, in the bonded portions, one sheet layer of the first sheet layer and the second sheet layer and the elastic sheet are melt-solidified, and the first sheet layer and the second sheet layer are bonded via the melt-solidified material. Therefore, the peel strength is higher than that obtained by bonding the first sheet layer and the second sheet layer only with a melt-solidified material of the elastic sheet. Further, since the layer that forms at least a surface opposite to the elastic sheet in the other sheet layer is not melt-solidified in the bonded portion, compared with the case where both the sheet layers are entirely melt-solidified, the laminated stretchable structure has excellent flexibility as a whole, also the layer that forms at least the surface opposite to the elastic sheet in the other sheet layer is not melt-solidified, and the melt-solidified material is covered with a fiber layer that is not melt-solidified. As a result, it is possible to prevent the appearance and touch feeling of the other sheet layer side from deteriorating.

In addition, "the layer that forms at least a surface opposite to the elastic sheet in the other sheet layer" includes both the cases of meaning a part in the thickness direction in the other sheet layer and meaning the whole of the thickness direction in the other sheet layer. In addition, the term "melting" includes not only melting of the entire fiber but also melting of the surrounding portion (including not only the sheath in composite fiber but also the surface layer side of single component fiber) while the fiber core (including the core of the composite fiber as well as the central part of the single component fiber) remains.

<Second Aspect>

In the disposable wearing article according to the first aspect, the other sheet layer is formed of a laminated nonwoven fabric having a melt layer that forms a surface on the elastic sheet and a non-melt layer that forms a surface opposite to the elastic sheet, in the bonded portion, the melt layer in the other sheet layer is melt-solidified, and the non-melt layer in the other sheet layer is not melt-solidified, and the first sheet layer and the second sheet layer are bonded via a melt-solidified material of the one sheet layer, a melt-solidified material of the elastic sheet, and a melt-solidified material of the melt layer in the other sheet layer at the bonded portion.

(Function and Effect)

The aspect in which the other sheet layer is not entirely melt-solidified is excellent in terms of flexibility and appearance, but as in the second aspect, when both the first sheet layer and the second sheet layer are melt-solidified, the bonding at the bonded portion becomes stronger. Furthermore, the entire second sheet layer is not melt-solidified, but the layer including a surface opposite to the elastic sheet is a non-melt layer, such that both the sheet layers are excellent in flexibility, appearance, and touch feeling, compared to those in which both the sheet layers are entirely melt-solidified.

Note that, in the laminated nonwoven fabric, fibers between layers are bonded by a known method (chemical bonding, physical entanglement, or physical bonding).

<Third Aspect>

In the disposable wearing article according to the second aspect, the fineness of constituent fibers of the melt layer is 1/2.5 to 1/1.7 times the fineness of constituent fibers of the non-melt layer.

(Function and Effect)

As described above, by having a sufficient difference in the fineness of the constituent fibers in the melt layer and the non-melt layer, the constituent fibers in the melt layer have relatively high specific surface area and is easily melted, and furthermore, the constituent fibers of the non-melt layer are relatively bulky and are not easily crushed. As a result, manufacturability is improved.

<Fourth Aspect>

In the disposable wearing article according to any one of the first to third aspects, the other sheet layer forms a surface exposed to the outside of a product.

(Function and Effect)

Since the layer that forms at least a surface opposite to the elastic sheet in the other sheet layer does not melt-solidified, when the other sheet layer forms a surface exposed to the outside of a product, the appearance of the product and the deterioration of the touch feeling can be prevented.

<Fifth Aspect>

In the disposable wearing article according to any one of the first to third aspects, the other sheet forms a surface exposed to the skin side of the product.

(Function and Effect)

Since the layer that forms at least a surface opposite to the elastic sheet in the other sheet layer does not melt-solidified, when the other sheet layer forms a surface exposed to the skin side in the product, the deterioration of the touch feeling on the inner side of the product can be prevented.

<Sixth Aspect>

In the disposable wearing article according to any one of the first to fifth aspects, the disposable wearing article is an underpants type disposable wearing article, and includes an outer member integrally provided from a front body to a back body or an outer member separately provided on the front body and the back body, an inner member attached to an intermediate portion in a width direction of the outer member and provided over both front and back sides of a crotch portion, a side seal portion in which both side portions of the outer member in the front body and both side portions of the outer member in the back body are bonded respectively, a waist opening, and a pair of right and left leg openings, and the outer member in at least one of the front body and the back body extends over at least a width direction range corresponding to between the side seal portions in a part of a range in a front-back direction, and the laminated stretchable structure is provided such that a stretchable direction is arranged in the width direction.

(Function and Effect)

Although underpants type disposable wearing articles are considered to be an article close to an underwear among disposable wearing articles, it is common to provide a wide stretchable region to ensure fitting, and it is particularly important to achieve both the peel strength and flexibility. Therefore, the laminated stretchable structure described above is suitable for such an underpants-type disposable wearing article.

Advantageous Effects of Invention

As described above, according to the present invention, there are advantages such as a disposable wearing article having a laminated stretchable structure excellent in peel strength and flexibility.

BRIEF DESCRIPTION OF DRAWINGS

FIG. 1 is a plan view (internal surface side) of an underpants-type disposable diaper in a spread state.

FIG. 2 is a plan view (external surface side) of an underpants-type disposable diaper in a spread state.

FIG. 3 is a plan view illustrating only a main part of an underpants-type disposable diaper in a spread state.

FIG. 4(a) is a cross-sectional view taken along line C-C of FIG. 1, and FIG. 4(b) is a cross-sectional view taken along line E-E of FIG. 1.

FIG. 5 is a cross-sectional view taken along line A-A of FIG. 1.

FIG. 6 is a cross-sectional view taken along line B-B of FIG. 1.

FIG. 7(a) is a plan view of a main part of an elastic region, FIG. 7(b) is a cross-sectional view taken along line D-D of FIG. 7(a), FIG. 7(c) is a cross-sectional view in a wearing state, and FIG. 7(d) is a cross-sectional view in a natural length state.

FIG. 8(a) is a trace diagram of a micrograph from a planar direction of an elastic region of a sample, FIG. 8(b) is a trace diagram of a high magnification micrograph from a planar direction, and FIG. 8(c) is a trace diagram of a high magnification micrograph from a perspective direction.

FIG. 9(a) is a plan view of a main part of an elastic region, FIG. 9(b) is a cross-sectional view taken along line D-D of FIG. 9(a), FIG. 9(c) is a cross-sectional view in a wearing state, and FIG. 9(d) is a cross-sectional view in a natural length state.

FIG. 10(a) is a trace diagram of a micrograph from a planar direction of an elastic region of a sample, FIG. 10(b) is a trace diagram of a high magnification micrograph from a planar direction, and FIG. 10(c) is a trace diagram of a high magnification micrograph from a perspective direction.

FIG. 11(a) is a plan view of a main part of a non-elastic region, FIG. 11(b) is a cross-sectional view taken along line D-D of FIG. 11(a), FIG. 11(c) is a cross-sectional view in a wearing state, and FIG. 11(d) is a cross-sectional view in a natural length state.

FIG. 12 is a trace diagram of a photograph of a non-elastic region of a sample.

FIG. 13 is an enlarged plan view of a main part of a non-elastic region.

FIG. 14 is a plan view illustrating various arrangement examples of a bonded portion.

FIG. 15 is a plan view (external surface side) of an underpants-type disposable diaper in a spread state.

FIG. 16(a) is a cross-sectional view taken along line C-C of FIG. 15, and FIG. 16(b) is a cross-sectional view taken along line E-E of FIG. 15.

FIG. 17 is a cross-sectional view schematically illustrating a cross section of a main part of an outer member expanded to some extent.

FIG. 18 is a cross-sectional view schematically illustrating a cross section of a main part of an outer member expanded to some extent.

FIG. 19 is a schematic diagram of an ultrasonic sealing device.

DESCRIPTION OF EMBODIMENTS

Hereinafter, from an example of an underpants-type disposable diaper, a disposable wearing article provided with a laminated stretchable structure will be described in detail. In addition, a dotted pattern portion in the cross-sectional view indicates a bonding means such as a hot melt adhesive.

FIGS. 1 to 6 illustrate an underpants-type disposable diaper. This underpants-type disposable diaper (hereinafter also simply referred to as a diaper) has an outer member 20 forming a front body F and a back body B, and an inner member 10 fixed and integrated to an inner surface of the outer member 20, and the inner member 10 is formed by interposing an absorber 13 between a liquid-pervious top sheet 11 and a liquid-impervious sheet 12. Upon manufacturing, after a back surface of the inner member 10 is bonded to an inner surface (upper surface) of the outer member 20 by a bonding means such as a hot melt adhesive, the inner member 10 and the outer member 20 are folded at the center in the front-back direction LD (longitudinal direction) which is a boundary between the front body F and the back body B, and both side portions thereof are bonded to each other by thermal welding, a hot melt adhesive, or the like to form a side seal portion 21. As a result, an underpants-type disposable diaper having a waist opening and a pair of left and right leg openings can be formed.

(Structure Example of Inner Member)

As illustrated in FIGS. 4 to 6, the inner member 10 has a structure in which the absorber 13 is interposed between the top sheet 11 and the liquid-impervious sheet 12 made of polyethylene or the like to absorb and retain excretion liquid that has permeated through the top sheet 11. The planar shape of the inner member 10 is not particularly limited, but generally it is a substantially rectangular shape as illustrated in FIG. 1.

As the liquid-pervious top sheet 11 covering a front surface side (skin side) of the absorber 13, a porous or nonporous nonwoven fabric, a porous plastic sheet, or the like is suitably used. For a raw material fiber forming a nonwoven fabric, in addition to synthetic fibers such as polyolefin type such as polyethylene or polypropylene, polyester type, polyamide type, etc., regenerated fibers such as rayon and cupra, and natural fibers such as cotton can be used, and a nonwoven fabric obtained by an appropriate processing method, such as a spun lace method, a spun bond method, a thermal bond method, a meltblown method, and a needle punch method can be used. In these processing methods, the spun lace method is excellent in terms of flexibility and drapability, and the thermal bond method is excellent in terms of bulkiness and softness. When a large number of through-holes are formed on the top sheet 11, urine and the like are quickly absorbed, and dry touch property is excellent. The top sheet 11 extends to back surface sides of the absorber 13 by wrapping up side edge portions of the absorber 13.

For the liquid-impervious sheet 12 covering a back surface side (non-skin contact side) of the absorber 13, a liquid-impervious plastic sheet such as polyethylene or polypropylene is used. In recent years, those having moisture permeability are preferably used from the viewpoint of prevention of stuffiness. This waterproof/moisture-pervious sheet is a microporous sheet obtained by stretching a sheet in one or two axial directions after forming the sheet by melt kneading an inorganic filler in a polyolefin resin such as polyethylene and polypropylene.

The absorber 13 is basically a known absorber, for example, accumulates of pulp fibers, assembly of filaments such as cellulose acetate, or nonwoven fabrics, and as necessary, super absorbent polymers can be mixed and fixed. The absorber 13 can be wrapped with a package sheet 14 having liquid permeability and liquid retention, such as crepe paper, as necessary, for shape and polymer retention and the like.

The shape of the absorber 13 is formed in a substantially hourglass shape having a narrowing portion 13N narrower than the front and back sides at a crotch portion. Although the size of the narrowing portion 13N can be determined as appropriate, the length in the front-back direction of the narrowing portion 13N can be set to about 20 to 50% of the entire length of the diaper, and the width of the narrowest portion is about 40 to 60% of the entire width of the absorber 13. In the case where such the narrowing portion 13N is provided, if the planar shape of the inner member 10 is substantially rectangular, a non-absorber side portion 17 without the absorber 13 is formed at a portion corresponding to the narrowing portion 13N of the absorber 13 in the inner member 10.

The liquid-impervious sheet 12 is folded back to the back surface side together with the top sheet 11 on both sides in the width direction of the absorber 13. As this liquid-impervious sheet 12, it is desirable to use an opaque sheet such that brown color of excreta, urine, and the like does not appear. As the opacification, a film obtained by internally adding a pigment or a filler such as calcium carbonate, titanium oxide, zinc oxide, white carbon, clay, talc, barium sulfate, or the like in a plastic is suitably used.

Three-dimensional gathers 90 fitting around the legs are formed on both sides of the inner member 10. As illustrated in FIGS. 5 and 6, the three-dimensional gather 90 includes a fixed portion 91, a main unit section 92, a fallen portion 93, and a free portion 94. The fixed portion 91 is fixed to a side portion of a back surface of the inner member 10. The main unit section 92 extends from the fixed portion 91 through a side of the inner member 10 to above a side portion of a front surface of the inner member 10. The fallen portion 93 is formed by fixing, by a hot melt adhesive 95b and the like, the front and back end portions of the main unit section 92 to the side portion of the surface (the top sheet 11 in the illustrated example) of the inner member 10 in a fallen state. The free portion 94 is formed by non-fixing between the fallen portions 93. Each of these portions is formed by a gather sheet 95 formed by folding a sheet such as a non-woven fabric into a duplicate sheet. The gather sheet 95 is attached to the entire front-back direction of the inner member 10, the fallen portion 93 is provided on a front side and a back side of the non-absorber side portion 17, and the free portion 94 extends on both front and back sides of the non-absorber side portion 17. Further, between the double gather sheets 95, an elongated gather elastic member 96 is disposed at a tip portion of the free portion or the like. As illustrated in FIG. 5, in a product state, the gather elastic member 96 is for making the free portion 94 stand up by elastic contraction force.

Although the main unit section 92 is not folded back, in the three-dimensional gather 90 illustrated in FIGS. 5 and 6, any known structure can be used, such that a portion on a root side of the main unit section obliquely stands toward the center in the width direction, and a portion on a tip side of the intermediate portion obliquely stands outward in the width direction (not illustrated).

As the gather elastic member 96, materials such as polystyrene-based rubber, polyolefin-based rubber, polyurethane-based rubber, polyester-based rubber, polyurethane, polyethylene, polystyrene, styrene butadiene copolymer, silicone, polyester, and the like which are usually used can be used. Further, in order to make it difficult to be seen from the outside, it is better that the fineness is set to 925 dtex or less, the tension is set to 150 to 350%, and the interval is set to 7.0 mm or less. As the gather elastic member 96, in addition to a thread-like shape as the illustrated example, a tape-shaped member having a certain width can be used.

Like the top sheet 11, for a raw material fiber forming the above-described gather sheet 95, in addition to synthetic fibers such as polyolefin type such as polyethylene or polypropylene, polyester type, polyamide type, etc., regenerated fibers such as rayon and cupra, and natural fibers such as cotton can be used, and a nonwoven fabric obtained by an appropriate processing method, such as a spun bond method, a thermal bond method, a meltblown method, and a needle punch method can be used. In particular, to prevent stuffiness, nonwoven fabric having low basis weight and excellent in air permeability is preferably used. Further, with respect to the gather sheet 95, in order to prevent permeation of urine or the like and also to prevent burning and improve the feeling to the skin (dry feel), it is desirable to use a water repellent treated nonwoven fabric coated with silicone type, paraffin metal type, alkylchromic chloride type water repellent, etc.

As illustrated in FIGS. 3 to 6, a back surface of the inner member 10 is bonded to an inner surface of the outer member 20 with a hot melt adhesive or the like in the inner and outer fixed region 10B (shaded region). The inner and outer fixed region 10B can be determined appropriately and can be substantially the whole width direction WD of the inner member 10. However, it is preferable that the both end portions in the width direction are not fixed to the outer member 20.

(Structure Example of Outer Member)

The outer member 20 extends from a side edge to a side of the absorber 13. As the illustrated example, in a crotch portion, the side edges of the outer member 20 may be located on the center side in the width direction form the side edges of the inner member 10 or may be located on the outer side in the width direction. Further, the outer member 20 includes a lower torso portion T which is a range in the front-back direction corresponding to a side seal portion 21 and an intermediate portion L which is a range in the front-back direction between the lower torso portion T of the front body F and the lower torso portion T of the back body B. In the outer member 20 of the illustrated example, except for the middle in the front-back direction of the intermediate portion L, as illustrated in FIGS. 2 and 4 to 6, an elastic sheet 30 is laminated between the first sheet layer 20A and the second sheet layer 20B, and as illustrated in FIG. 7, the outer member 20 has a laminated stretchable structure 20X in which the first sheet layer 20A and the second sheet layer 20B are bonded through the through-holes 31 penetrating the elastic sheet 30 at a large number of bonded portions 40 arranged at intervals, and an extending direction ED is the width direction WD. The first sheet layer 20A and the second sheet layer 20B may be indirectly bonded via the elastic sheet 30, not through the through-hole 31 of the elastic sheet 30. The planar shape of the outer member 20 is formed by a recessed leg around line 29 so as to form leg openings at both side edges in the width direction of the intermediate portion L and has a shape resembling an hourglass as a whole. The outer members 20 may be formed separately for the front body F and the back body B and may be arranged such that those are spaced apart in the front-back direction LD at a crotch portion.

In the example illustrated in FIGS. 1 and 2, the laminated stretchable structure 20X extends to a waist end region 23. When the laminated stretchable structure 20X is used in the waist end region 23, tightening of the waist end region 23 may be insufficient. Therefore, as illustrated FIGS. 15 and 16, without providing the laminated stretchable structure 20X in the waist end region 23, a stretchable structure by a conventional elongated waist elastic member 24 can be provided if necessary. The waist elastic member 24 is an elongated elastic member such as a plurality of rubber threads arranged at intervals in the front-back direction LD and provides stretching force so as to tighten around the waist of a wearer. The waist elastic member 24 is not arranged substantially as a single bundle with a close interval, but three or more, preferably five or more waist elastic members 24 are disposed at intervals of about 3 to 8 mm so as to form a predetermined stretching zone. A stretch rate at the time of fixing the waist elastic member 24 can be appropriately determined, but it can be set to about 230 to 320% for adults usually. Although a rubber thread is used for the waist elastic member 24 in the illustrated example, another elongated elastic member such as flat rubber or the like may be used. Although not illustrated, it is also possible to provide the elastic sheet 30 at the waist end region 23 and to provide the elongated waist elastic member 24 at a position overlapping with the elastic sheet 30 so as to have a stretchable structure by the both elastic members. Also, in the illustrated example, the elongated elastic member extending along the leg opening is not provided at the edge portion of the leg opening of the outer member 20. However, at a portion overlapping with the elastic sheet 30 in the edge portion or an elongated elastic member may be provided in place of the elastic sheet 30 of the edge portion.

In another example, although not illustrated, appropriate deformation is possible, such that the laminated stretchable structure 20X is not provided in the intermediate portion L between the lower torso portion T of the front body F and the lower torso portion T of the back body B, the stretchable structure 20X is continuously provided in the front-back direction LD from the inside of the lower torso portion T of the front body F to the inside of the lower torso portion T of the back body B through the intermediate portion L, or the laminated stretchable structure 20X is provided only on one of the front body F and the back body B.

The constituent materials of the first sheet layer 20A and the second sheet layer 20B are not particularly limited as long as they are in the form of a sheet, but it is preferable to use a nonwoven fabric from the viewpoints of air permeability and flexibility. In the nonwoven fabric, a raw material fiber thereof is not particularly limited. Examples of the nonwoven fabric can include synthetic fibers such as polyolefin type such as polyethylene and polypropylene, polyester type, and polyamide type, regenerated fibers such as rayon and cupra, natural fibers such as cotton, and mixed fibers and composite fibers in which two or more of these are used. Further, the nonwoven fabric may be manufactured by any processing. Examples of the processing method include known methods such as a spun lace method, a spun bond method, a thermal bond method, a meltblown method, a needle punch method, an air-through method, and a point bond method. Further, a part or the whole of the first sheet layer 20A and the second sheet layer 20B may be a pair of layers in which a single material is folded back to face each other. For example, as in the illustrated example, in the waist end region 23, the constituent material located on the outer side is the second sheet layer 20B, and the folded portion 20C folded back to the internal surface side at a waist opening edge is the first sheet layer 20A, and the elastic sheet 30 is interposed therebetween. In the other portions, the constituent material located on the inner side is the first sheet layer 20A, the constituent material located on the outer side is the second sheet layer 20B, and the elastic sheet 30 can be interposed therebetween. It is obvious that the constituent material of the first sheet layer 20A and the constituent material of the second sheet layer 20B can be individually provided over the entire front-back direction LD, and without folding back the constituent materials, the elastic sheet 30 may be interposed between the constituent material of the first sheet layer 20A and the constituent material of the second sheet layer 20B.

The elastic sheet 30 is not particularly limited, and may be a stretchable nonwoven fabric in addition to an elastic film as long as the sheet is made of a thermoplastic resin having elasticity. As the elastic sheet 30, besides a non-porous film, it is also possible to use a film having many holes or slits for ventilation. In particular, in the elastic sheet 30, the tensile strength in the width direction WD (stretchable direction ED, MD direction) is preferably 8 to 25 N/35 mm, the tensile strength in the front-back direction LD (direction XD orthogonal to the stretchable direction, CD direction) is preferably 5 to 20 N/35 mm, the tensile elongation in the width direction WD is preferably 450 to 1050%, and the tensile elongation in the front-back direction LD is preferably 450 to 1400%. The thickness of the elastic sheet 30 is not particularly limited, but it is preferably about 20 to 40 μm.

Although the shape of each of the bonded portions 40 and the through-holes 31 in a natural length state can be determined as appropriate, it can be an arbitrary shape such as a perfect circle (refer to FIGS. 7 and 8), an ellipse, a polygon such as a triangle, a rectangle (refer to FIGS. 9 to 12) and a rhombus (refer to FIG. 13(b)), a convex lens shape (refer to FIG. 13(a)), a concave lens shape (refer to FIG. 13(c)), a star shape, a cloud shape, and the like. Although the size of each bonded portion is not particularly limited, the maximum length is preferably 0.5 to 3.0 mm, particularly preferably 0.7 to 1.1 mm, and the maximum width 40x is preferably 0.1 to 3.0 mm, particularly preferably 0.1 to 1.1 mm in the case where the shape is long in the direction XD orthogonal to the stretchable direction.

The size of each bonded portion 40 may be determined appropriately, but if it is too large, the hardness of the bonded portion 40 exerts an influence on the feeling, and if it is too small, a joined area is small, and materials are insufficiently adhered. Therefore, in the usual case, the area of each bonded portion 40 is preferably about 0.14 to 3.5 mm$^2$. The area of an opening of each through-hole 31 may be equal to or more than that of the bonded portion 40 because the bonded portion 40 is formed through the through-hole 31, and it is preferable to set to about 1 to 1.5 times the area of the bonded portion 40. The area of the opening of the through-hole 31 means a value not in a state of the elastic sheet 30 alone and a value in a state of being integrated with the first sheet layer 20A and the second sheet layer 20B and in a state of natural length and means the minimum value in the case where the area of the opening of the through-hole 31 is not uniform in the thickness direction like that it is different on the front and back of the elastic sheet 30.

Although the planar arrangement of the bonded portion 40 and the through-hole 31 can be appropriately determined, a regularly repeated plane arrangement is preferred. In addition to the regularly repeated plane arrangement such as an oblique lattice shape as illustrated in FIG. 14(a), a hexagonal lattice shape (also referred to as a zigzag shape) as illustrated in FIG. 14(b), a square lattice shape as illustrated in FIG. 14(c), a rectangular lattice shape as illustrated in FIG. 14(d), and a parallel lattice shape as illustrated in FIG. 14(e) (arrangement in which two groups of many parallel oblique direction rows are provided so as to cross each other) (including those inclined at an angle of less than 90° with respect to the stretchable direction ED), a group of the bonded portion 40 (the group may be regularly or irregularly arranged, and may be a pattern or a letter shape) can be regularly repeated.

In the case where the first sheet layer 20A and the second sheet layer 20B in the bonded portion 40 is bonded through the through-hole 31 formed on the elastic sheet 30, it is desirable that the first sheet layer 20A and the second sheet layer 20B be not bonded to the elastic sheet 30 at least in a portion other than between the first sheet layer 20A and the second sheet layer 20B in the bonded portion 40.

As illustrated in FIGS. 17 and 18, in the bonded portion 40, the first sheet layer 20A and the elastic sheet 30 are melt-solidified, a layer forming at least a surface opposite to the elastic sheet 30 in the second sheet layer 20B is not melt-solidified, and the first sheet layer 20A and the second sheet layer 20B are bonded at the bonded portion 40 via a melt-solidified product m1 of the first sheet layer 20A and a melt-solidified product m2 of the elastic sheet 30.

That is, in the bonded portion 40, the first sheet layer 20A and the elastic sheet 30 are melt-solidified, and the first sheet layer 20A and the second sheet layer 20B are bonded via the melt-solidified materials m1 and m2. As a result, the peel strength is higher than that of the first sheet layer 20A and the second sheet layer 20B bonded by only the melt-solidified material m2 of the elastic sheet 30. In this case, the melt-solidified material m2 of the elastic sheet 30 may be completely infiltrated between fibers of the second sheet layer 20B in the bonded portion 40 as illustrated in FIG. 17 (FIGS. 17(a) and 17(b)) and may be partially infiltrated (FIG. 17(c)). Further, the melt-solidified material m1 of the first sheet layer 20A may not infiltrate between fibers of the second sheet layer 20B (FIGS. 17(a) and 17(c)) and may be partially infiltrated (FIG. 17(b)).

Further, since the layer that forms at least a surface opposite to the elastic sheet 30 in the second sheet layer 20B is not melt-solidified in the bonded portion 40, compared with the case where both of the sheet layers 20A and 20B are melt-solidified, the laminated stretchable structure 20X has excellent flexibility as a whole. In addition, since the layer that forms at least a surface opposite to the elastic sheet 30 in the second sheet layer 20B is not melt-solidified, it is possible to prevent the appearance (covered by a fiber layer that is not melt-solidified) and touch feeling on the second sheet layer 20B side from deteriorating. In particular, in the illustrated example, the second sheet layer 20B forms a surface exposed to the outside of a product, such that appearance of the product outer surface and deterioration of the touch feeling can be prevented.

The bonding of the first sheet layer 20A and the second sheet layer 20B in the bonded portion 40 can be performed by pressurizing and heating the bonded position by bonding means by material welding such as heat sealing or ultrasonic sealing with the elastic sheet 30 interposed between the first sheet layer 20A and the second sheet layer 20B. The laminated stretchable structure manufacturing apparatus illustrated in FIG. 19 is an example. That is, in the time of forming the bonded portion 40, the laminated stretchable structure manufacturing apparatus feeds the first sheet layer 20A, the elastic sheet 30, and the second sheet layer 20B between an anvil roll 60 having a protruding portion 60a formed in a pattern of the bonded portion 40 on the outer surface and an ultrasonic horn 61. At this time, for example, by setting a feed moving speed of the elastic sheet 30 on the upstream side by a feed drive roll 63 and a nip roll 62 to be slower than a conveying speed of the elastic sheet 30 on the downstream side of the anvil roll 60 and the ultrasonic horn 61, the elastic sheet 30 is elongated in the MD direction (machine direction, flow direction) at a predetermined stretch rate in a path from a nip position by the feed drive roll 63 and the nip roll 62 to a sealing position by the anvil roll 60 and the ultrasonic horn 61. The stretch rate of the elastic sheet 30 can be set by selecting a speed difference between the anvil roll 60 and the feed drive roll 63 and can be set to, for example, about 300% to 500%. The reference sign 62 denotes a nip roll. The first sheet layer 20A, the elastic sheet 30, and the second sheet layer 20B, which are fed between the anvil roll 60 and the ultrasonic horn 61, are laminated in this order, pressurized between the protruding portion 60a and the ultrasonic horn 61, and heated by ultrasonic vibration energy of the ultrasonic horn 61. As a result, the first sheet layer 20A and the elastic sheet 30 are melted, and the layer forming at least the surface opposite to the elastic sheet 30 in the second sheet layer 20B is not melted. Thereby, simultaneously with the formation of the through-hole 31 in the elastic sheet 30, the first sheet layer 20A and the second sheet layer 20B are bonded through the through-holes 31. Therefore, in this case, by selecting the size, shape, separation distance, arrangement pattern in the roll length direction and roll circumferential direction, etc. of the protruding portion 60a of the anvil roll 60, the area ratio of the bonded portion 40 can be selected.

The reason why the through-hole 31 is formed is not necessarily clear, but it is considered that the portion of the elastic sheet 30, which corresponds to the protruding portion 60a of the anvil roll 60, melts, and detached from the surroundings to form a hole. At this time, as illustrated in FIGS. 7(a), 9(a) and 11(a), the portion of the elastic sheet 30 between the adjacent through-holes 31 aligned in the extending direction ED is cut from the portion of both sides in the extending direction by the through-hole 31 and loses support on both sides in a contraction direction. Therefore, the portion shrinks in a range, in which the continuity in the direction orthogonal to the contraction direction is secured, until the center side of the direction XD orthogonal to the extending direction ED balances with the center side of the extending direction, and the through-hole 31 expands in the extending direction ED. Then, in the case where the bonded portion 40 is formed with a pattern in which the elastic sheet 30 has a portion linearly continue along the extending direction ED like the stretchable region 80 to be described later, as illustrated in FIGS. 7(a) and 9(a), when shrinking to a natural length by cutting to an individual product, the length of the extending direction ED of the enlarged portion of the through-hole 31 shrinks until a gap between the through-hole 31 and the bonded portion 40 is not formed. On the other hand, in the case where the bonded portion 40 is formed with a pattern in which the elastic sheet 30 does not linearly continue along the extending direction ED like a non-stretchable region 70 to be described later, as illustrated in FIG. 11(a), when shrinking to a natural length by cutting to an individual product, shrinkage hardly occurs. Therefore, a large gap remains between the through-hole 31 and the bonded portion 40.

To melt-solidify the first sheet layer 20A and the elastic sheet 30, and not to melt-solidify the layer forming at least a surface opposite to the elastic sheet 30 in the second sheet layer 20B, at least one of (a) to (c) can be adopted:

(a) making the melting point of the constituent fiber of the first sheet layer 20A lower than the melting point of the constituent fiber of the second sheet layer 20B;

(b) making the fiber basis weight of the first sheet layer 20A lower than the fiber basis weight of the second sheet layer 20B; and (c) making the fineness of the constituent fibers of the first sheet layer 20A lower than the fineness of the constituent fibers of the second sheet layer 20B If there is a sufficient difference in fabric basis weight and fineness, depending on the heating temperature and heating time, the first sheet layer 20A can receive sufficient energy for melting, and the second sheet layer 20B can receive only insufficient energy for melting. Accordingly, the first sheet layer 20A and the elastic sheet 30 can be melt-solidified, and the layer forming at least a surface opposite to the elastic sheet 30 in the second sheet layer 20B can be prevented from being melt-solidified. In particular, it is preferable to combine the above (a) with at least one of the above (b) and (c).

The melting points (in the case of composite fibers, the melting point of the component with a lower melting point) of the constituent fiber of the first sheet layer 20A and the second sheet layer 20B are preferably about 85 to 190° C., and particularly preferably about 150 to 190° C., and the elastic sheet 30 has a melting point of about 80 to 180° C., particularly preferably about 85 to 145° C. When the melting point of the constituent fiber of the first sheet layer 20A is lower than the melting point of the constituent fiber of the second sheet layer 20B, the difference between the constituent fiber melting point of the first sheet layer 20A and the constituent fiber melting point of the second sheet layer 20B is preferably about 60 to 90° C.

The fiber basis weight of the first sheet layer 20A and the second sheet layer 20B is preferably about 10 to 25 g/m². Further, when the fiber basis weight of the first sheet layer 20A is made lower than the fiber basis weight of the second sheet layer 20B, the fiber basis weight of the first sheet layer 20A is preferably 1/5 to 1/1.7 of the fiber basis weight of the second sheet layer 20B.

The fineness of the constituent fibers of the first sheet layer 20A and the second sheet layer 20B is preferably about 1.5 to 2.5 dtex. When the fineness of the constituent fiber of the first sheet layer 20A is lower than the fineness of the constituent fiber of the second sheet layer 20B, the fineness of the constituent fiber of the first sheet layer 20A is preferably about 1/2.5 to 1/1.7 times the fineness of the constituent fiber of the second sheet layer 20B. As described above, by having a sufficient difference in the fineness of the constituent fibers in the first sheet layer 20A and the non-melt layer, the specific surface area of the constituent fiber of the first sheet layer 20A is relatively high and is easily melted, and furthermore, the constituent fiber of the non-melt layer is relatively bulky and is not easily crushed. As a result, manufacturability is improved.

As an example, a combination using a spunbonded nonwoven fabric with fineness of 1.0 dtex and a basis weight of 13 g/m$^2$ as the first sheet layer 20A, and a spunbonded nonwoven fabric with fineness of 2.0 dtex and a basis weight of 17 g/m$^2$ as the second sheet layer 20B is exemplified. As another example, a combination using a spunbonded nonwoven fabric with fineness of 2.0 dtex and a basis weight of 13 g/m$^2$ as the first sheet layer 20A, and an air through nonwoven fabric with fineness of 2.0 dtex and a basis weight of 17 g/m$^2$ as the second sheet layer 20B is exemplified.

Each of the first sheet layer 20A and the second sheet layer 20B may be a single-layer nonwoven fabric (a nonwoven fabric in which the fiber material, basis weight, fineness, etc. hardly change in the thickness direction) or a laminated nonwoven fabric having a plurality of nonwoven fabric layers. In the laminated nonwoven fabric, fibers between layers are bonded by a known method (chemical bonding, physical entanglement, or physical bonding).

The aspect in which the entire second sheet layer 20B does not melt-solidify is excellent in terms of flexibility and appearance, and the second sheet layer 20B is preferably a laminated nonwoven fabric having a melt layer ML that forms a surface on the elastic sheet 30 and a non-melt layer UL that forms a surface opposite to the elastic sheet 30. That is, in the bonded portion 40, the melt layer ML in the second sheet layer 20B is melt-solidified, and the non-melt layer UL in the second sheet layer 20B is not melt-solidified. When the first sheet layer 20A and the second sheet layer 20B are bonded at the bonded portion 40 via the melt-solidified material m1 of the first sheet layer 20A, the melt-solidified product m2 of the elastic sheet 30, and a melt-solidified product m3 of the melt layer ML in the second sheet layer 20B, the bonding of the bonded portion 40 becomes further strong. Furthermore, the entire second sheet layer 20B is not melt-solidified, but the layer including a surface opposite to the elastic sheet 30 is a non-melt layer UL, such that both the sheet layers 20A and 20B are excellent in flexibility, appearance, and touch feeling, compared to those in which the entire sheet layer is melt-solidified.

In this case, as illustrated in FIG. 18(*a*), the melt solidified material m3 of the melt layer ML in the second sheet layer 20B may not infiltrate into the non-melt layer UL and may infiltrate as illustrated in FIG. 18(*b*).

To melt-solidify the melt layer ML and not to melt-solidify the non-melt layer UL, at least one of the following (a) to (c) can be adopted:

(a) making the melting point of the constituent fiber of the melt layer ML lower than the melting point of the constituent fiber of the non-melt layer UL;

(b) making the fiber basis weight of the melt layer ML lower than the fiber basis weight of the non-melt layer UL; and (c) making the fineness of the constituent fiber of the melt layer ML lower than the fineness of the constituent fiber of the non-melt layer UL.

When there is a sufficient difference in fiber weight and fineness, the melt layer ML can receive sufficient energy for melting, and the non-melt layer UL can receive insufficient energy for melting, depending on the heating temperature and heating time. Accordingly, the above-described melt-solidification becomes possible. In particular, it is preferable to combine the above (a) with at least one of the above (b) and (c).

The melting points of the constituent fibers of the melt layer ML and the non-melt layer UL (the melting point of the component having a lower melting point in the case of a composite fiber) is preferably about 85 to 190° C., particularly preferably about 150 to 190° C. When the melting point of the constituent fiber of the melt layer ML is set lower than the melting point of the constituent fiber of the non-melt layer UL, it is preferable that the difference between the constituent fiber melting point of the melt layer ML and the constituent fiber melting point of the non-melt layer UL be 60 to 90° C.

Each of the fiber basis weights of the melt layer ML and the non-melt layer UL are preferably about 7 to 20 g/m$^2$. When the fiber basis weight of the melt layer ML is made lower than the fiber basis weight of the non-melt layer UL, it is preferable that the fiber basis weight of the melt layer ML be about 1/2.5 to 1/1.7 times the fiber basis weight of the non-melt layer UL.

The fineness of the constituent fibers of the melt layer ML and the non-melt layer UL is preferably about 1.0 to 2.5 dtex. When the fineness of the constituent fiber of the melt layer ML is set lower than the fineness of the constituent fiber of the non-melt layer UL, the fineness of the constituent fiber of the melt layer ML is preferably 1/2.5 to 1/1.2 times the fineness of the constituent fiber of the non-melt layer UL. As described above, by having a sufficient difference in the fineness of the constituent fibers in the melt layer ML and the non-melt layer UL, the constituent fibers in the melt layer ML have relatively high specific surface area and is easily melted, and furthermore, the constituent fiber of the non-melt layer UL is relatively bulky and are not easily crushed. As a result, manufacturability is improved.

The thicknesses of the melt layer ML and the non-melt layer UL in the second sheet layer 20B can be determined as appropriate. In normal cases, it is preferable that the thickness of the melt layer ML in the second sheet layer 20B be about 0.3 to 1.0 mm. Further, the thickness of the non-melt layer UL in the second sheet layer 20B is preferably about 0.7 to 2.0 mm. Further, the thickness of the melt layer ML is preferably 1/3 to 1/1.5 times the thickness of the non-melt layer UL.

As an example, a laminated nonwoven fabric in which a melt layer is a spun bond layer with fineness of 1.0 dtex and a basis weight of 7 g/m$^2$, and the non-melt layer is a spun bond layer with fineness of 1.8 dtex and a basis weight of 13 g/m$^2$ can be used as the second sheet layer. As another example, a laminated nonwoven fabric in which a melt layer is a spun bond layer with fineness of 1.5 dtex and a basis weight of 10 g/m$^2$, and a non-melt layer is a spun bond layer with fineness of 1.5 dtex and a basis weight of 20 g/m$^2$ can be used as the second sheet layer.

In FIGS. 17 and 18, the melt-solidified material m1 of the first sheet layer 20A, the melt-solidified material m2 of the elastic sheet 30, and the melt-solidified material m3 of the melt layer ML in the second sheet layer 20B are not mixed (or may not be entrapped), but may be partially or wholly intermingled (or entrapped).

Contrary to the examples illustrated in FIGS. 17 and 18, it is also preferable that, in the bonded portion 40, the second sheet layer 20B and the elastic sheet 30 be melt-solidified, a layer forming at least a surface opposite to the elastic sheet 30 in the first sheet layer 20A be not melt-solidified, and the first sheet layer 20A and the second sheet layer 20B be bonded at the bonded portion 40 via the melt-solidified material of the second sheet layer 20B and the melt-solidified material of the elastic sheet 30 (not illustrated). In this case, since, in the first sheet layer 20A that forms a surface exposed to the skin side of a product does not melt-solidify the layer that forms at least a surface opposite to the elastic sheet 30, the deterioration of the touch feeling of the inner surface of the product can be prevented.

(Stretchable Region)

A region having the laminated stretchable structure 20X in the outer member 20 has a stretchable region that can expand and contract in the width direction WD. In the stretchable region 80, the elastic sheet 30 has a portion 32 linearly continuing along the width direction WD, and the elastic sheet 30 contracts in the width direction WD due to contraction force of the elastic sheet 30 and can be stretched in the width direction WD. More specifically, with the elastic sheet 30 extended in the width direction WD, the first sheet layer 20A and the second sheet layer 20B are bonded via the through-hole 31 of the elastic sheet 30 with a space in the width direction WD and the front-back direction LD (direction XD orthogonal to the extending direction) orthogonal to the width direction WD. By forming a large number of bonded portions 40, the laminated stretchable structure 20X is formed, and by arranging the through-holes 31 such that the elastic sheet 30 has a linearly continuous portion along the width direction WD in the stretchable region 80, whereby such elasticity can be imparted.

In a natural length state, as illustrated in FIGS. 7(d) and 9(d), in the stretchable region 80, the first sheet layer 20A and the second sheet layer 20B between the bonded portions 40 bulge in directions away from each other, shrinkage wrinkles 25 extending in the front-back direction LD are formed, and the shrinkage wrinkles 25 are stretched even in a wearing state extended to some extent in the width direction WD, but those remain, as illustrated in FIGS. 7(c) and 9(c). In addition, as the illustrated example, when the first sheet layer 20A and the second sheet layer 20B are not bonded to the elastic sheet 30 at least a space other than between the first sheet layer 20A and the second sheet layer 20B in the bonded portion 40, as can be seen from the FIGS. 7(c) and 9(d) assuming the wearing state and FIGS. 7(a), 7(b), 9(a), and 9(b) assuming a spread state of the first sheet layer 20A and the second sheet layer 20B, in these states, a gap is formed between through-holes 31 in the elastic sheet 30 and the bonded portions 40, and even if a material of the elastic sheet 30 is a non-porous film or sheet, air permeability is imparted by this gap. In addition, in the natural length state indicated in FIGS. 7(d) and 9(d), the through-hole 31 is narrowed by contraction of the elastic sheet 30, and a gap is not formed almost between the through-hole 31 and the bonded portion 40. Note that the state of the shrinkage wrinkles 25 in a wearing state and a natural length state can be found also in FIGS. 8 and 10.

It is desirable that the elastic limit elongation of the stretchable region 80 in the width direction WD is 200% or more (preferably 265 to 295%). The elastic limit elongation of the stretchable region 80 is substantially determined by the stretch rate of the elastic sheet 30 at the time of manufacture. On the basis of this, the elastic limit elongation rate decreases due to a factor of inhibiting shrinkage in the width direction WD. The main cause of such inhibition is a ratio of the length 40x of the bonded portion 40 to a unit length in the width direction WD, and the elastic limit elongation decreases as this ratio increases. In the usual case, since the length 40x of the bonded portion 40 is correlated with the area ratio of the bonded portion 40, the elastic limit elongation of the stretchable region 80 can be adjusted by the area ratio of the bonded portion 40.

The extension stress of the stretchable region 80 can be adjusted mainly by a sum of the width 32w of the portion 32 where the elastic sheet 30 linearly continues along the width direction WD. The width 32w of the portion 32 in which the elastic sheet 30 linearly continues along the width direction WD is equal to a distance 31d in the front-back direction LD of the through-hole 31 in contact with both side edges of the continuous portion 32. The distance 31d between the through-holes 31 is equal to a distance 40d in the front-back direction LD of the bonded portion 40 in contact with the both side edges of the continuous portion when the length 31y of the through-hole 31 in the front-back direction LD and the length 40y of the bonded portion 40 in the front-back direction LD are equal (in the case of adopting the above-described simultaneous forming method of the through-hole 31 and the bonded portion 40 etc.). Therefore, in this case, depending on the ratio of the length 40y of the bonded portion 40 per unit length in the front-back direction LD, the extension stress of the stretchable region 80 can be adjusted. In the usual case, since the length 40y of the bonded portion 40 has a correlation with the area ratio of the bonded portion 40, the elongation stress of the stretchable region 80 can be adjusted by the area ratio of the bonded portion 40. The elongation stress of the stretchable region 80 can be taken as an indication of elongation stress when the stretchable region 80 is elongated to 50% of the elastic limit.

The area ratio of the bonded portion 40 and the area of each bonded portion 40 in the stretchable region 80 can be appropriately determined, but in the usual case, it is preferable to be within the following range.

The area of the bonded portion 40: 0.14 to 3.5 $mm^2$ (particularly 0.14 to 1.0 $mm^2$)

The area ratio of the bonded portion 40: 1.8 to 19.1% (particularly 1.8 to 10.6%)

In this way, since the elastic limit elongation and elongation stress of the stretchable region 80 can be adjusted by the area of the bonded portion 40, as illustrated in FIG. 15, a plurality of regions having different area ratios of the bonded portion 40 in the stretchable region 80 is provided to change the fitting according to a site. In the example illustrated in FIG. 15, the area ratio of the bonded portion 40 is higher in the region 81 extending obliquely along the root of the leg in the front body F and the edge region 82 of the leg opening than those in the other regions, and therefore the elongation stress is weak, and the regions flexibly expand and contract. In addition, the area ratio of the bonded portion 40 is also higher in an iliac opposing region 83 and an edge region 82 of the leg opening in the back body B than those in the other regions, and therefore the elongation stress is weak, and the regions flexibly expand and contract.

(Non-Stretchable Region)

As illustrated in FIG. 15, the non-stretchable region 70 can be provided on at least one side in the width direction of the stretchable region 80 in the region of the outer member 20 having the laminated stretchable structure 20X. The arrangement of the stretchable region 80 and the non-stretchable region 70 can be appropriately determined. In the case of the outer member 20 of the underpants-type disposable diaper according to the present example, since the part overlapping with the absorber 13 is a region unnecessary to expand and contract, as the illustrated example, a part or all of the portion overlapping with the absorber 13 (it is desirable to include nearly the entire inner and outer fixed regions 10B) is preferably the non-stretchable region 70. It is obvious that the non-stretchable region 70 can be provided from a region overlapping with the absorber 13 to a region not overlapping with the absorber 13 located in the width direction WD or the front-back direction LD, and the non-stretchable region 70 can be provided only in the region not overlapping with the absorber 13.

In the non-stretchable region 70, although the elastic sheet 30 continues in the width direction WD, the elastic sheet 30 does not have a linearly continuous portion along the width direction WD due to the presence of the through-hole 31. Therefore, with the elastic sheet 30 extended in the width direction WD, the first sheet layer 20A and the second sheet layer 20B are bonded to each other through the through-hole 31 of the elastic sheet 30 with a space therebetween in the width direction WD and the front-back direction LD orthogonal thereto. Even if the whole of the laminated stretchable structure 20X including both the stretchable region 80 and the non-stretchable region 70 is formed by forming a large number of bonded portions 40, as illustrated in FIG. 11, the elastic sheet 30 does not linearly continue along the width direction WD in the non-stretchable region 70, such that contraction force of the elastic sheet 30 hardly acts on the first sheet layer 20A and the second sheet layer 20B, and elasticity almost disappears, and elastic limit elongation approaches 100%. In such non-stretchable region 70, the first sheet layer 20A and the second sheet layer 20B are bonded at a large number of bonded portions 40 arranged with a space therebetween, and the bonded portion 40 is not continuous. Therefore, a decrease in flexibility is prevented. In other words, the stretchable region 80 and the non-stretchable region 70 can be formed in accordance with the presence or absence of a portion where the elastic sheet 30 does not linearly continue along the width direction WD. In addition, continuity of the elastic sheet 30 still remains in the non-stretchable region 70, as understood from FIG. 12, since independent cut pieces of the elastic sheet 30 are not left, and wrinkles are not formed, appearance is extremely excellent, and the air permeability in the thickness direction by the through-hole 31 is secured. In the non-stretchable region 70, the elastic limit elongation in the width direction WD is preferably 120% or less (preferably 110% or less, more preferably 100%).

Although the arrangement pattern of the through-holes 31 in the elastic sheet 30 in the non-stretchable region 70 can be determined as appropriate, as illustrated in FIG. 11, if the center interval 31e of the through-hole 31 in the front-back direction LD is set to be shorter than the length 31y of the through-hole 31 in the front-back direction LD, it is possible to almost completely eliminate the linear continuity in the width direction WD while maintaining the continuity of the elastic sheet 30, and the appearance is also preferable as illustrated in FIG. 12. In this case, it is more preferable that a center interval 31f of the through-hole 31 in the width direction WD is shorter than the length 31x of the through-hole 31 in the width direction WD.

In the usual case, in particular, when the elongation stress when the elastic sheet 30 is expanded four times in the width direction WD is 4 to 12 N/35 mm, in the state where the non-stretchable region 70 is extended to the elastic limit in the width direction WD, it is preferable that the center interval 31e of the through-hole 31 in the front-back direction LD is 0.4 to 2.7 mm, and the length 31y of the through-hole 31 in the front-back direction LD is 0.5 to 3.0 mm, particularly 0.7 to 1.1 mm. In addition, the center interval 31f of the through-hole 31 in the width direction WD is preferably 0.5 to 2 times, more preferably 1 to 1.2 times the length 31y of the through-hole 31 in the front-back direction LD, and the length 31x of the through-hole 31 in the width direction WD is preferably 1.1 to 1.8 times the center interval 31f of the through-hole 31 in the width direction WD, particularly 1.1 to 1.4 times. In a state in which the non-stretchable region 70 is extended to the elastic limit in the width direction WD (in other words, in a state in which the first sheet layer 20A and the second sheet layer 20B are fully developed), the center interval 31f of the through-hole 31 in the width direction WD is equal to the center interval 40f of the bonded portion 40 in the width direction WD, the center interval 31e of the through-hole 31 in the front-back direction LD is equal to the center interval 40e of the bonded portion 40 in the front-back direction LD, and the length 31y of the through-hole 31 in the front-back direction LD is equal to the length 40y of the bonded portion 40 in the front-back direction LD.

In the non-stretchable region 70, the first sheet layer 20A, the second sheet layer 20B, and the elastic sheet 30 are not bonded except between the first sheet layer 20A and the second sheet layer 20B in the bonded portion 40. When a gap formed by separating a peripheral edge of the through-hole 31 of the elastic sheet 30 and the bonded portion 40 from both sides in the width direction of the bonded portion 40 in a natural length state, even if the material of the elastic sheet 30 is a non-porous film or sheet, it is preferable since air permeability is constantly added by this gap. In the case of adopting the above-described simultaneous forming method of the through-hole 31 and the bonded portion 40, this state is formed naturally irrespective of the shape of the bonded portion 40 or the like.

The shape of each bonded portion 40 and the through-hole 31 in the natural length state is not particularly limited, but it is desirable that the area be small from the viewpoint of flexibility. To eliminate the linear continuity in the width direction WD of the elastic sheet 30, a shape that is long in the front-back direction LD is desirable. Therefore, an elliptical shape, a rectangular shape (refer to FIGS. 11 and 13(d)), a rhombus (refer to FIG. 13(b)), or a convex lens shape (refer to FIG. 13(a)), and a concave lens shape (refer to FIG. 13(c)) that are long in the front-back direction LD are preferable. However, if corners are acute as in a rhombus, the elastic sheet 30 tends to break. In contrast, the convex lens shape is preferable in that the welding of the bonded portion 40 is stabilized, and the concave lens shape is preferable in that the area can be further reduced.

The area ratio of the bonded portion 40 and the area of the each bonded portion 40 in the non-stretchable region can be appropriately determined, but in the usual case, it is preferable that the area is within the following range, since the non-stretchable region 70 is not hardened due to the small area of each bonded portion 40 and the low area ratio of each bonded portion 40.

The area of the bonded portion 40: 0.10 to 0.75 mm$^2$ (particularly 0.10 to 0.35 mm$^2$)

The area ratio of the bonded portion 40: 4 to 13% (especially 5 to 10%)

In this way, the elastic limit elongation of the non-stretchable region 70 can be changed by the arrangement pattern of the through-holes 31, the dimensions of each through-hole 31, and the center distance. Therefore, although not illustrated, these can be made different at a plurality of positions within the stretchable region 80 or between a plurality of the non-stretchable regions 70. For example, it is preferable to set the elastic limit elongation in the non-stretchable region 70 of the front body F larger than the elastic limit elongation in the non-stretchable region 70 of the back body B.

Although the non-stretchable region 70 has a portion linearly continuing along the width direction WD similarly to the stretchable region, the elastic limit elongation is remarkably low because the area ratio of the bonded portion is higher than the stretchable region. Therefore, specifically a structure in which the elastic limit elongation is equal to or less than 130%, a structure in which the non-stretchable region 70 is cut at one or a plurality of places in the width direction WD like a conventional stretchable structure using rubber thread, and other structure to suppress elasticity can be used.

<Others>

In addition to underpants-type disposable diapers, the laminated stretchable structure 20X described above can be applied to other stretchable portions and the like such as the lower torso and fastening tape of tape type disposable diapers, three-dimensional gathers, and flat gathers that are widely used for absorbent articles in general. Depending on the application site, the stretchable direction can be the width direction, the front-back direction, or both the width direction and the front-back direction.

<Explanation of Terms Used Herein>

The following terms in the specification have the following meanings unless otherwise specified in the specification.

"Front body" and "back body" mean front and back portions, respectively, with the center in the front-back direction of an underpants-type disposable diaper as a boundary. In addition, a crotch portion means a front-back direction range including the center in the front-back direction of an underpants-type disposable diaper, and in the case where an absorber has a narrowing portion, it means a range in the front-back direction of the portion having the narrowing portion.

"Elastic limit elongation" means the elongation of the elastic limit in the extending direction ED (in other words, the state in which the first sheet layer and the second sheet layer are completely developed), and the length at the elastic limit is expressed as a percentage in the case where a natural length is assumed to be 100%.

"Area ratio" means a ratio of a target portion to a unit area. A total area of the target portion (for example, the bonded portion 40, an opening of the through-hole 31, a vent hole) in the target region (for example, the stretchable region 80, the non-stretchable region 70, a main elastic portion, and a cushioning elastic portion) is expressed as a percentage. In particular, the "area ratio" in the region having the stretchable structure means an area ratio in a state where it is extended to the elastic limit in the extending direction ED. In the case where a large number of target portions are provided at intervals, it is desirable to set the target region to a size such that ten or more target portions are included and obtain the area ratio.

"Stretch rate" means the value when the natural length is taken as 100%.

"Basis weight" is measured as follows. After preliminary drying a sample or a test piece, the sample or the test piece is left in a test chamber or equipment in the standard state (the test location is at a temperature of 23±1° C. and with a relative humidity of 50±2%) to be constant weight. The preliminary drying refers to making a sample or a test piece a constant weight in an environment at a temperature of 100° C. For fibers with an official moisture regain of 0.0%, preliminary drying may not be performed. A sample of dimensions of 100 mm×100 mm is cut using a template for sampling (100 mm×100 mm) from a test piece in a constant weight. The basis weight is set by weighing the sample, multiplying by 100, and calculating the weight per one square meter.

"Thickness" of an absorber is measured using a thickness measuring instrument (Peacock, large dial gauge type, model J-B (measurement range 0 to 35 mm) or model K-4 (measurement range 0 to 50 mm)) manufactured by Ozaki Seisakusho Co., Ltd., and a sample and the thickness measuring instrument are set to be horizontal.

"Thickness" other than the above is automatically measured under the conditions of a load of 0.098 $N/cm^2$ and a pressing area of 2 $cm^2$ using an automatic thickness measuring device (KES-G5 handy compression measuring program).

"Tensile strength" and "tensile elongation (breaking elongation)" mean values obtained by measuring with an initial chuck distance (gauge line distance) of 50 mm and a tensile speed of 300 ram/min according to JIS K7127: 1999 "Test method of plastic-tensile properties-" except that the test piece is formed into a rectangular shape having a width of 35 mm×a length of 80 mm. As a tensile tester, for example, AUTOGRAPHAGS-G100N manufactured by SHIMADZU corporation can be used.

"Elongation stress" means a tensile stress (N/35 mm) measured when extending in the elastic region by a tensile test in which the initial chuck distance (distance between the gauge marks) is 50 mm, and the tensile speed is 300 mm/min according to JIS K7127: 1999 "Test method of plastic-tensile properties -", and the degree of elongation can be appropriately determined depending on the test target. It is preferable that the test piece has a rectangular shape with a width of 35 mm and a length of 80 mm or more, but when a test piece with a width of 35 mm cannot be cut out, a test piece is formed with a width that can be cut out, and the measured value is 35 mm in width. Even if the target area is small, and it is not possible to collect a sufficient test piece, as long as comparing the magnitude of the elongation stress, even a small test specimen can be compared at least as long as a test piece of the same size is used. As a tensile tester, for example, AUTOGRAPHAGS-G100N manufactured by SHIMADZU corporation can be used.

"Spread state" means a flatly spread state without shrinkage or slackness.

The dimension of each part means the dimension in the spread state, not the natural length state, unless otherwise stated.

When environmental conditions in tests and measurements are not described, the tests and measurements shall be carried out in a test room or apparatus in a standard state (a temperature of 23±1° C. and a relative humidity of 50±2% at the test location).

INDUSTRIAL APPLICABILITY

As long as having the above-described laminated stretchable structure, the present invention can be applied to all disposable wearing articles such as tape-type and pad-type disposable diapers, sanitary napkins, disposable wearing articles for swimming and dabbling in water, in addition to the above-described underpants-type disposable diaper.

REFERENCE SIGNS LIST 10 inner member
10B inner and outer fixed region
11 top sheet
12 liquid-impervious sheet
13 absorber
13N narrowing portion
14 package sheet
17 non absorber side part
20 outer member
20A first sheet layer
20B second sheet layer
20C folded back portion
20X laminated stretchable structure
20Y non-laminated stretchable structure region
21 side seal portion
23 waist end region
24 waist elastic member
25 shrinkage wrinkle
29 leg around line
30 elastic sheet
31 through-hole
40 bonded portion
70 non-stretchable region
80 stretchable region
90 three-dimensional gather
93 fallen part
94 free part
95 gather sheet
96 gather elastic member
B back body
ED stretchable direction
F front body
L intermediate portion
LD front-back direction
T lower torso portion
WD width direction
m1 melt-solidified material of first sheet layer 20A
m2 melt-solidified material of elastic sheet 30
ML melt layer
UL non-melt layer
m3 melt-solidified material of melt layer ML

The invention claimed is:

1. A disposable wearing article, comprising a laminated stretchable structure, in which an elastic sheet of thermoplastic resin is laminated between a first sheet layer made of nonwoven fabric and a second sheet layer made of nonwoven fabric, and the first sheet layer and the second sheet layer are bonded through through-holes formed on the elastic sheet at a large number of bonded portions arranged at intervals,
   wherein, in the bonded portions, one of the first sheet layer and the second sheet layer comprises a one sheet layer and the other of the first sheet layer and the second sheet layer comprises an other sheet layer,
   wherein, the one sheet layer and the elastic sheet are each melt-solidified in whole in a thickness direction in the bonded portions, and a layer forming at least a surface opposite to the elastic sheet in the other sheet layer is not melt-solidified in the bonded portions, and
   wherein the first sheet layer and the second sheet layer are bonded via a melt-solidified material of the one sheet layer and a melt-solidified material of the elastic sheet at the bonded portions.

2. The disposable wearing article according to claim 1, wherein the other sheet layer is formed of a laminated nonwoven fabric having a melt layer that forms a surface on the elastic sheet and a non-melt layer that forms a surface opposite to the elastic sheet,
   in the bonded portion, the melt layer in the other sheet layer is melt-solidified, and the non-melt layer in the other sheet layer is not melt-solidified, and
   the first sheet layer and the second sheet layer are bonded via a melt-solidified material of the one sheet layer, a melt-solidified material of the elastic sheet, and a melt-solidified material of the melt layer in the other sheet layer at the bonded portion.

3. The disposable wearing article according to claim 2, wherein fineness of constituent fibers of the melt layer is 1/2.5 to 1/1.7 times fineness of constituent fibers of the non-melt layer.

4. The disposable wearing article according to claim 1, wherein the other sheet layer forms a surface exposed to the outside of a product.

5. The disposable wearing article according to claim 1, wherein the other sheet forms a surface exposed on a skin side of the product.

6. The disposable wearing article according to claim 1, which is an underpants type disposable wearing article, comprising an outer member integrally provided from a front body to a back body or an outer member separately provided on the front body and the back body, an inner member attached to an intermediate portion in a width direction of the outer member and provided over both front and back sides of a crotch portion, a side seal portion in which both side portions of the outer member in the front body and both side portions of the outer member in the back body are bonded respectively, a waist opening, and a pair of right and left leg openings, and
   wherein the outer member in at least one of the front body and the back body extends over at least a width direction range corresponding to between the side seal portions in a part of a range in a front-back direction, and the laminated stretchable structure is provided such that a stretchable direction is arranged in the width direction.

7. The disposable wearing article according to claim 2, wherein the other sheet layer forms a surface exposed to the outside of a product.

8. The disposable wearing article according to claim 3, wherein the other sheet layer forms a surface exposed to the outside of a product.

9. The disposable wearing article according to claim 2, wherein the other sheet forms a surface exposed on a skin side of the product.

10. The disposable wearing article according to claim 3, wherein the other sheet forms a surface exposed on a skin side of the product.

11. The disposable wearing article according to claim 2, which is an underpants type disposable wearing article, comprising an outer member integrally provided from a front body to a back body or an outer member separately provided on the front body and the back body, an inner member attached to an intermediate portion in a width direction of the outer member and provided over both front and back sides of a crotch portion, a side seal portion in which both side portions of the outer member in the front body and both side portions of the outer member in the back body are bonded respectively, a waist opening, and a pair of right and left leg openings, and wherein the outer member in at least one of the front body and the back body extends over at least a width direction range corresponding to between the side seal portions in a part of a range in a front-back direction, and the laminated stretchable structure is provided such that a stretchable direction is arranged in the width direction.

12. The disposable wearing article according to claim 3, which is an underpants type disposable wearing article, comprising an outer member integrally provided from a front body to a back body or an outer member separately provided on the front body and the back body, an inner member attached to an intermediate portion in a width direction of the outer member and provided over both front and back sides of a crotch portion, a side seal portion in which both side portions of the outer member in the front body and both side portions of the outer member in the back body are bonded respectively, a waist opening, and a pair of right and left leg openings, and wherein the outer member in at least one of the front body and the back body extends over at least a width direction range corresponding to between the side seal portions in a part of a range in a front-back direction, and the laminated stretchable structure is provided such that a stretchable direction is arranged in the width direction.

13. The disposable wearing article according to claim 4, which is an underpants type disposable wearing article, comprising an outer member integrally provided from a front body to a back body or an outer member separately provided on the front body and the back body, an inner member attached to an intermediate portion in a width direction of the outer member and provided over both front and back sides of a crotch portion, a side seal portion in which both side portions of the outer member in the front body and both side portions of the outer member in the back body are bonded respectively, a waist opening, and a pair of right and left leg openings, and wherein the outer member in at least one of the front body and the back body extends over at least a width direction range corresponding to between the side seal portions in a part of a range in a front-back direction, and the laminated stretchable structure is provided such that a stretchable direction is arranged in the width direction.

14. The disposable wearing article according to claim 5, which is an underpants type disposable wearing article, comprising an outer member integrally provided from a front body to a back body or an outer member separately provided on the front body and the back body, an inner member attached to an intermediate portion in a width direction of the outer member and provided over both front and back sides of a crotch portion, a side seal portion in which both side portions of the outer member in the front body and both side portions of the outer member in the back body are bonded respectively, a waist opening, and a pair of right and left leg openings, and wherein the outer member in at least one of the front body and the back body extends over at least a width direction range corresponding to between the side seal portions in a part of a range in a front-back direction, and the laminated stretchable structure is provided such that a stretchable direction is arranged in the width direction.

* * * * *